(12) United States Patent
Orth et al.

(10) Patent No.: US 11,918,768 B2
(45) Date of Patent: Mar. 5, 2024

(54) MEDICAL DEVICES FOR FLUID DELIVERY AND METHODS OF USE AND MANUFACTURE

(71) Applicant: Encompass Vascular, Inc., San Jose, CA (US)

(72) Inventors: Jean C. Orth, Morgan Hill, CA (US); Zaya Tun, Livermore, CA (US); Robert G. Quintos, Newark, CA (US)

(73) Assignee: Encompass Vascular, Inc., San Jose, CA (US)

( * ) Notice: Subject to any disclaimer, the term of this patent is extended or adjusted under 35 U.S.C. 154(b) by 0 days.

(21) Appl. No.: 18/345,746

(22) Filed: Jun. 30, 2023

(65) Prior Publication Data

US 2023/0347020 A1 Nov. 2, 2023

Related U.S. Application Data

(63) Continuation of application No. 17/937,287, filed on Sep. 30, 2022, now Pat. No. 11,759,550, which is a continuation of application No. PCT/US2022/027049, filed on Apr. 29, 2022.

(60) Provisional application No. 63/240,812, filed on Sep. 3, 2021, provisional application No. 63/203,472, filed on Jul. 23, 2021, provisional application No.
(Continued)

(51) Int. Cl.
*A61M 25/10* (2013.01)
*A61M 25/00* (2006.01)

(52) U.S. Cl.
CPC .......... *A61M 25/10* (2013.01); *A61M 25/005* (2013.01); *A61F 2250/0067* (2013.01); *A61M 2025/0024* (2013.01); *A61M 2025/105* (2013.01); *A61M 2025/1086* (2013.01)

(58) Field of Classification Search
CPC ................ A61M 25/10; A61M 25/005; A61M 2025/0024; A61M 2025/105; A61M 2025/1086; A61F 2250/00676
See application file for complete search history.

(56) References Cited

U.S. PATENT DOCUMENTS

| 4,693,243 A | 9/1987 | Buras |
| 4,782,834 A | 11/1988 | Maguire et al. |

(Continued)

FOREIGN PATENT DOCUMENTS

| EP | 1825824 B1 | 11/2009 |
| EP | 1339448 B1 | 2/2010 |

(Continued)

OTHER PUBLICATIONS

Orth; U.S. Appl. No. 62/953,342; Balloon-based infusion catheters and methods of use in the lung; filed Dec. 24, 2019.
(Continued)

*Primary Examiner* — Laura A Bouchelle
*Assistant Examiner* — John A Doubrava
(74) *Attorney, Agent, or Firm* — Shay Glenn LLP; Thomas M. Zlogar

(57) ABSTRACT

Medical devices and methods for delivering fluid. The medical devices include one or more needles for delivering fluid. The methods may optionally include expanding an expandable member such as an inflatable member to expand an expandable scaffold outward toward a lumen wall. The devices may include one or both of one or more spine securing members or one or more needle alignment members.

21 Claims, 22 Drawing Sheets

Related U.S. Application Data

63/202,933, filed on Jun. 30, 2021, provisional application No. 63/202,721, filed on Jun. 22, 2021, provisional application No. 63/182,701, filed on Apr. 30, 2021.

(56) References Cited

U.S. PATENT DOCUMENTS

| | | | |
|---|---|---|---|
| 5,049,132 A | 9/1991 | Shaffer et al. | |
| 5,336,178 A * | 8/1994 | Kaplan | A61M 29/02 604/913 |
| 5,425,709 A * | 6/1995 | Gambale | A61M 25/104 604/103.05 |
| 5,464,395 A | 11/1995 | Faxon et al. | |
| 5,562,620 A | 10/1996 | Klein et al. | |
| 5,681,281 A | 10/1997 | Vigil et al. | |
| 5,693,029 A | 12/1997 | Leonhardt | |
| 5,713,863 A | 2/1998 | Vigil et al. | |
| 5,772,629 A | 6/1998 | Kaplan | |
| 5,810,767 A | 9/1998 | Klein et al. | |
| 5,843,033 A | 12/1998 | Ropiak | |
| 6,159,196 A * | 12/2000 | Ruiz | A61M 25/00 604/500 |
| 6,283,947 B1 | 9/2001 | Mirzaee | |
| 6,283,951 B1 | 9/2001 | Flaherty et al. | |
| 6,302,870 B1 | 10/2001 | Jacobsen et al. | |
| 6,599,267 B1 | 7/2003 | Ray et al. | |
| 6,625,486 B2 | 9/2003 | Lundkvist et al. | |
| 6,656,155 B2 | 12/2003 | Freyman | |
| 6,692,466 B1 | 2/2004 | Chow | |
| 6,808,518 B2 | 10/2004 | Wellman et al. | |
| 6,991,617 B2 | 1/2006 | Hektner et al. | |
| 7,273,469 B1 | 9/2007 | Chan et al. | |
| 7,419,497 B2 | 9/2008 | Muni et al. | |
| 7,569,032 B2 | 8/2009 | Naimark et al. | |
| 7,572,270 B2 | 8/2009 | Johnson | |
| 7,837,670 B2 | 11/2010 | Barath | |
| 7,850,644 B2 | 12/2010 | Gonzalez et al. | |
| 7,901,451 B2 | 3/2011 | Savage et al. | |
| 8,043,257 B2 | 10/2011 | Nguyen et al. | |
| 8,070,694 B2 | 12/2011 | Galdonik et al. | |
| 8,439,867 B2 | 5/2013 | Staskin | |
| 8,579,956 B2 | 11/2013 | Hossainy | |
| 8,740,849 B1 | 6/2014 | Fischell et al. | |
| 9,056,185 B2 | 6/2015 | Fischell et al. | |
| 9,108,030 B2 | 8/2015 | Braga | |
| 9,131,983 B2 | 9/2015 | Fischell et al. | |
| 9,237,925 B2 | 1/2016 | Fischell et al. | |
| 9,333,327 B2 | 5/2016 | Setliff, III et al. | |
| 9,339,630 B2 | 5/2016 | Cook et al. | |
| 9,370,644 B2 | 6/2016 | Rocha-Singh | |
| 9,393,386 B2 | 7/2016 | Schneider et al. | |
| 9,468,443 B2 | 10/2016 | Elgaard et al. | |
| 9,504,491 B2 | 11/2016 | Callas et al. | |
| 9,757,543 B2 | 9/2017 | Raghavan et al. | |
| 10,086,175 B2 | 10/2018 | Torres et al. | |
| 10,118,016 B2 | 11/2018 | Schwartz et al. | |
| 10,124,153 B2 | 11/2018 | Feig et al. | |
| 10,172,729 B2 | 1/2019 | Fulkerson et al. | |
| 10,350,392 B2 | 7/2019 | Fishell et al. | |
| 10,433,821 B2 | 10/2019 | Gunday et al. | |
| 10,589,070 B2 | 3/2020 | Herman et al. | |
| 10,653,442 B2 | 5/2020 | Anand et al. | |
| 10,765,838 B2 | 9/2020 | Nishio et al. | |
| 11,071,847 B1 | 7/2021 | Orth et al. | |
| 11,167,111 B1 | 11/2021 | Orth et al. | |
| 11,491,312 B2 | 11/2022 | Orth et al. | |
| 11,654,268 B2 | 5/2023 | Orth | |
| 11,654,269 B2 | 5/2023 | Orth | |
| 11,759,550 B2 | 9/2023 | Orth et al. | |
| 2003/0032929 A1 | 2/2003 | McGuckin | |
| 2004/0127475 A1 | 7/2004 | New et al. | |
| 2005/0137615 A1 | 6/2005 | Mapes et al. | |
| 2005/0203612 A1 | 9/2005 | Bhat et al. | |
| 2005/0261662 A1 | 11/2005 | Palasis et al. | |
| 2007/0213761 A1 | 9/2007 | Murphy et al. | |
| 2008/0051866 A1 | 2/2008 | Chen et al. | |
| 2010/0168714 A1 | 7/2010 | Burke et al. | |
| 2011/0166516 A1 | 7/2011 | Orr | |
| 2011/0184384 A1 | 7/2011 | DaValian et al. | |
| 2013/0060229 A1 | 3/2013 | Herman et al. | |
| 2017/0007310 A1 | 1/2017 | Rajagopalan et al. | |
| 2017/0035990 A1 | 2/2017 | Swift | |
| 2017/0100141 A1 | 4/2017 | Morero et al. | |
| 2018/0193078 A1 | 7/2018 | Rajagopalan et al. | |
| 2020/0060723 A1 | 2/2020 | Walzman | |
| 2020/0060942 A1 * | 2/2020 | Rajagopalan | A61B 5/6852 |
| 2020/0261693 A1 | 8/2020 | Walzman | |
| 2022/0088350 A1 | 3/2022 | Orth et al. | |
| 2022/0105108 A1 | 4/2022 | Seward | |
| 2022/0265292 A1 * | 8/2022 | Carpenter | A61M 25/1002 |

FOREIGN PATENT DOCUMENTS

| | | | |
|---|---|---|---|
| EP | 2328650 B1 | 4/2016 | |
| EP | 3192473 A1 | 7/2017 | |
| EP | 2654874 B1 | 4/2018 | |
| EP | 3558424 A1 | 10/2019 | |
| EP | 2838598 B1 | 1/2020 | |
| EP | 3065799 B1 | 1/2020 | |
| WO | WO2021/133966 A1 | 7/2021 | |
| WO | WO2022/072698 A1 | 4/2022 | |
| WO | WO2022/182598 A1 | 9/2022 | |
| WO | WO2022/232589 A1 | 11/2022 | |

OTHER PUBLICATIONS

Seward et al.; Adventitial guanethidine (MMS-008) in comparison to ethanol and a prior formulation of guanethidine (MMS-007) for renal denervation: preclinical norepinephrine and histopathology results; Journal of the American College of Cardiology; 74(13S): B595; Oct. 2019.

Stefanadis et al.; Chemical denervation of the renal artery with vincristine for the treatment of resistant arterial hypertension: first-in-man application; Hellinic Journal of Cardiology; 54; pp. 318-321; Jul. 2013.

Thomas; Restenosis treatment: 16 pages; retrieved from the internet (https://web.archive.org/web/20210804122825/https://www.news-medical.net/health/Restenosis-Treatment.aspx) 16 pages; on Jul. 15, 2022.

Orth; U.S. Appl. No. 18/301,159 entitled "Medical devices for fluid delivery and methods of use and manufacture," filed Apr. 14, 2023.

* cited by examiner

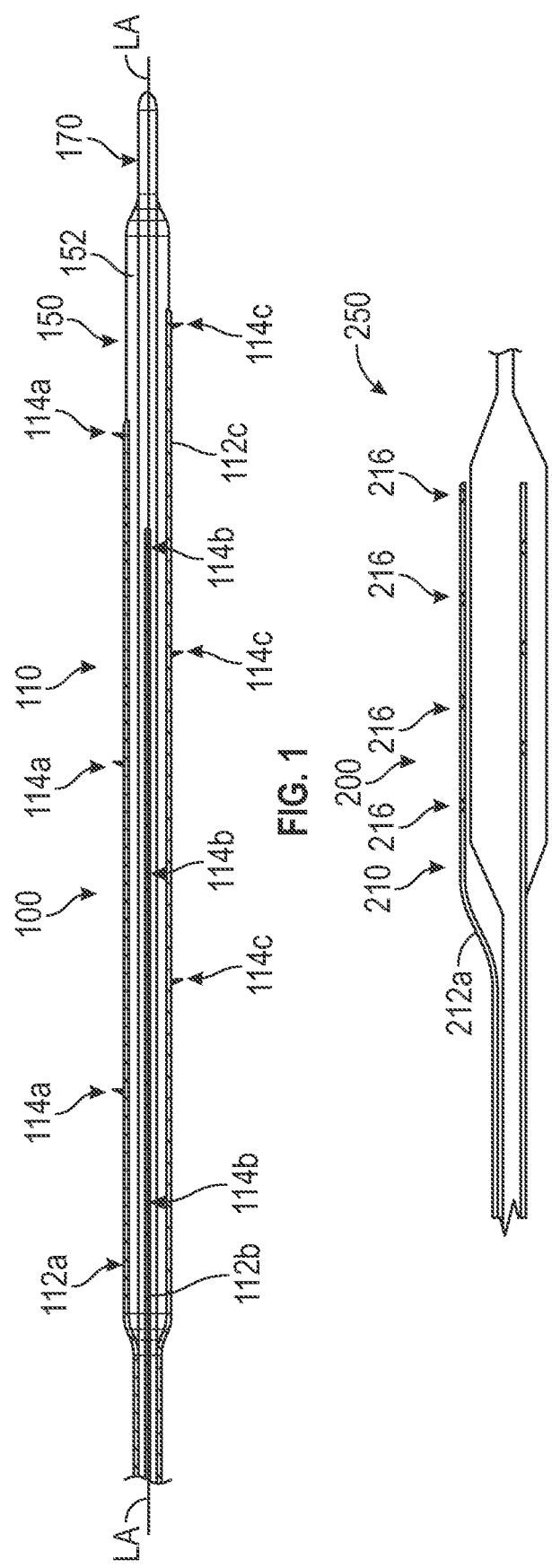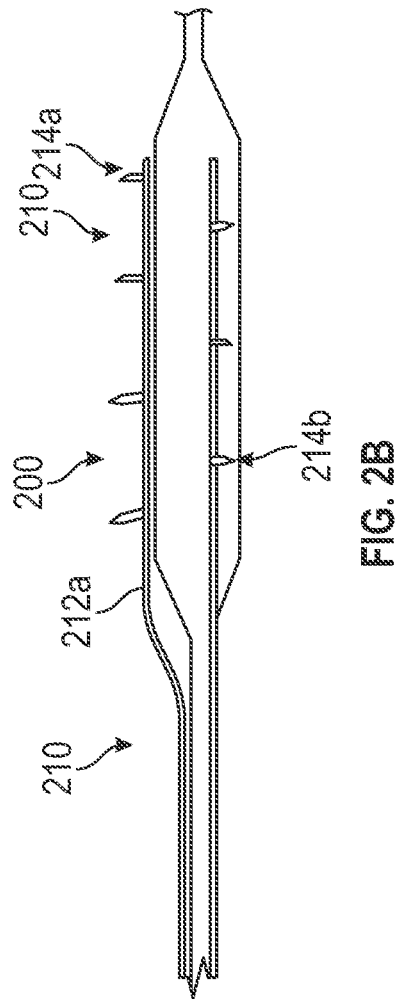

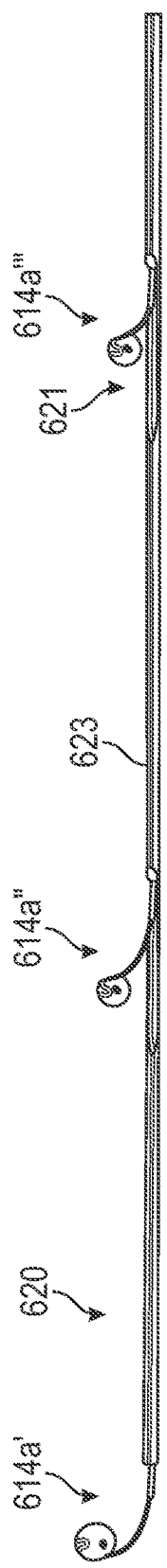
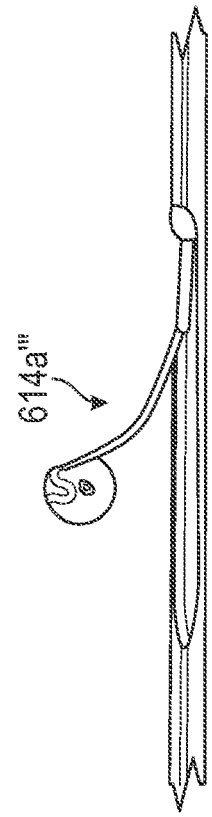
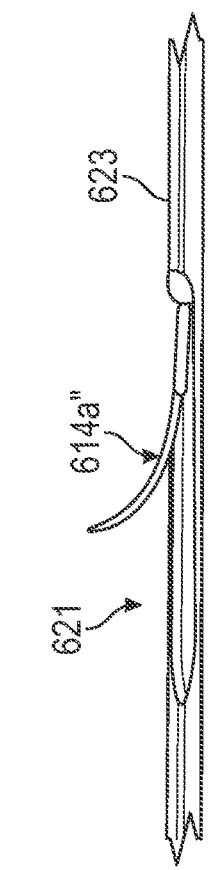
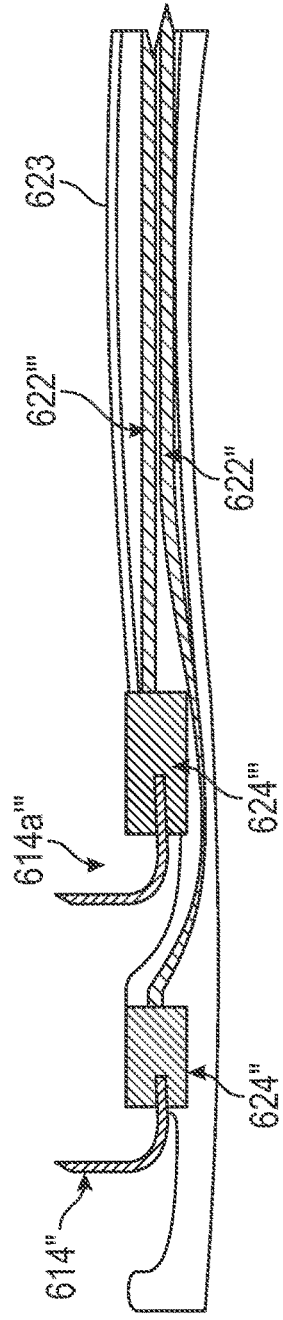
FIG. 6A
FIG. 6B
FIG. 6C
FIG. 6D

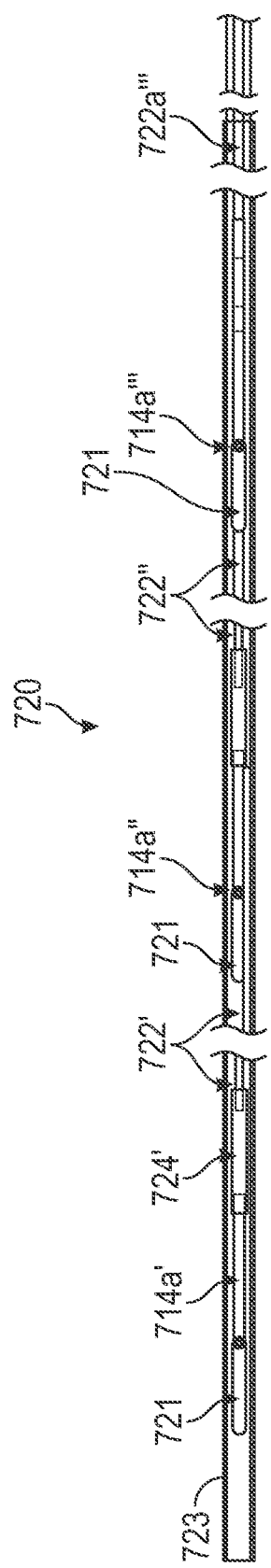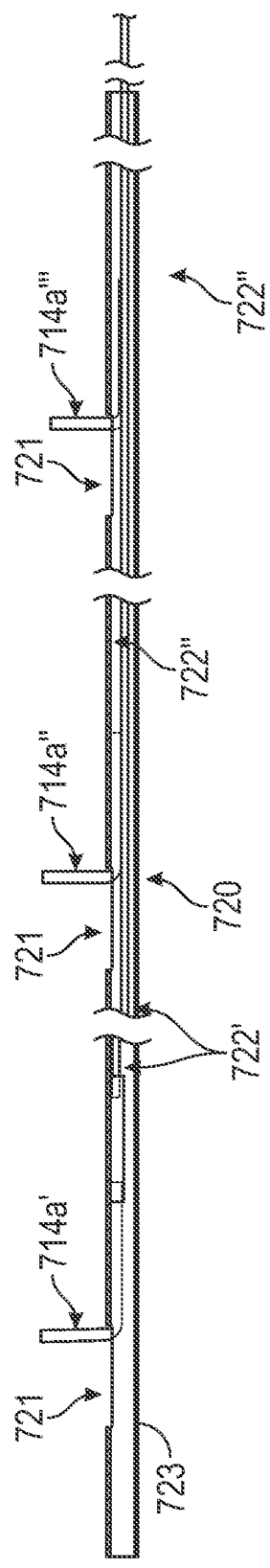
FIG. 7A
FIG. 7B

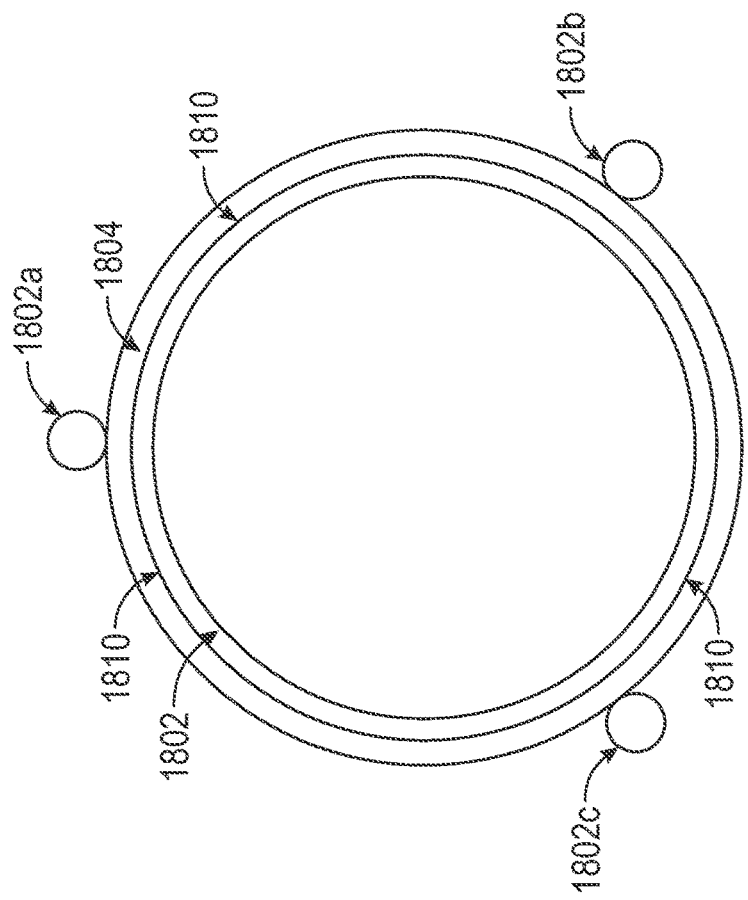
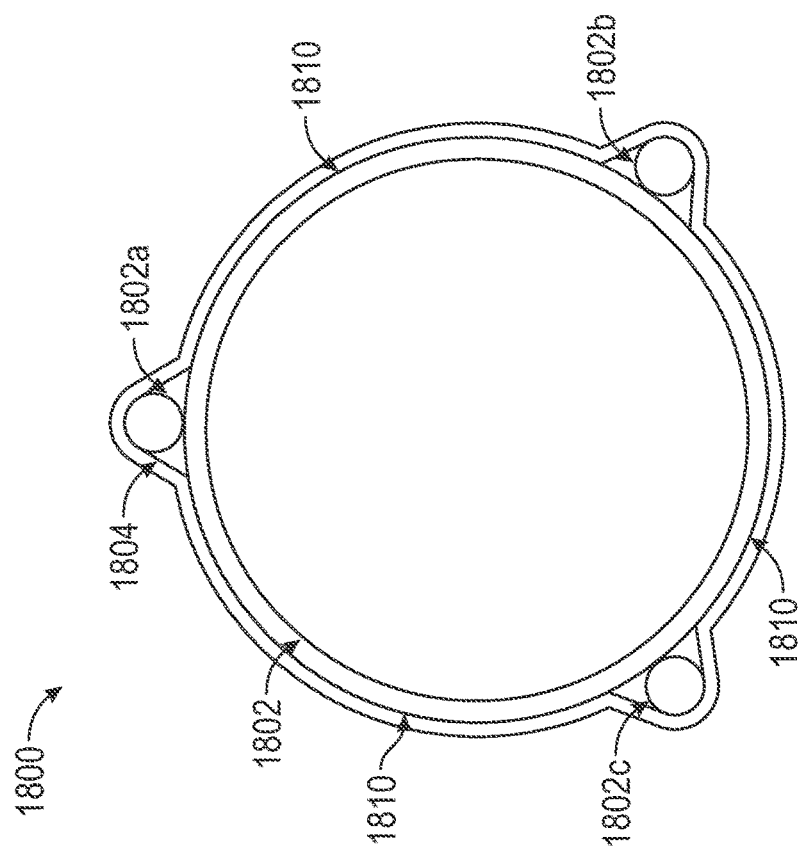
FIG. 18D
FIG. 18C

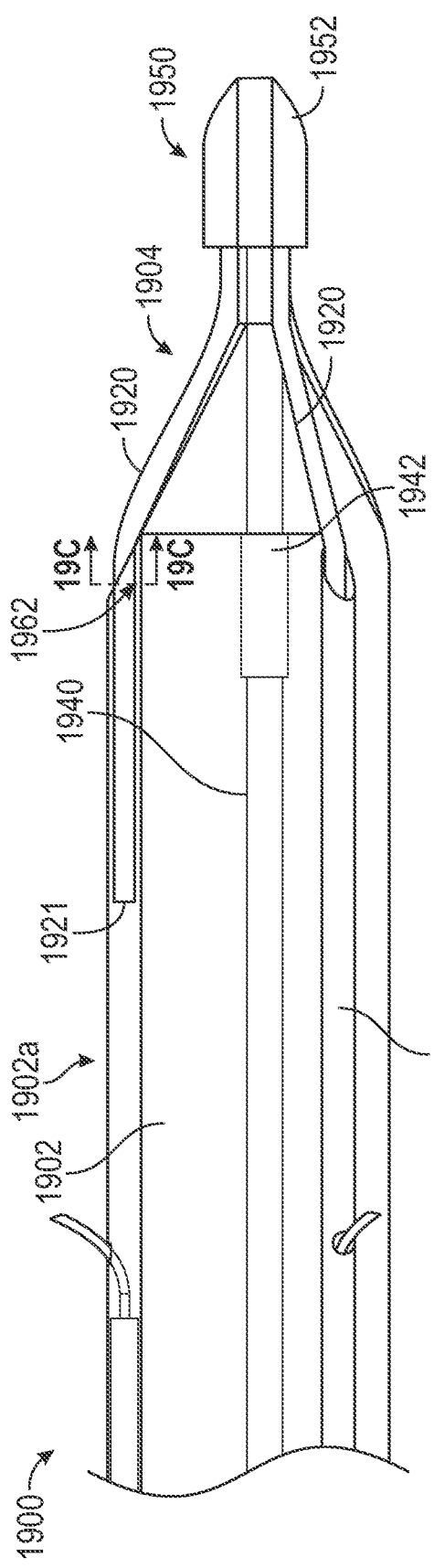
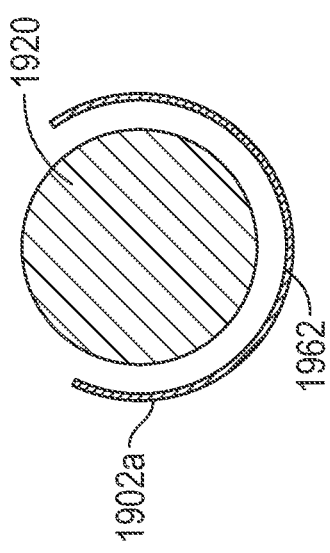
FIG. 19A
FIG. 19B
FIG. 19C

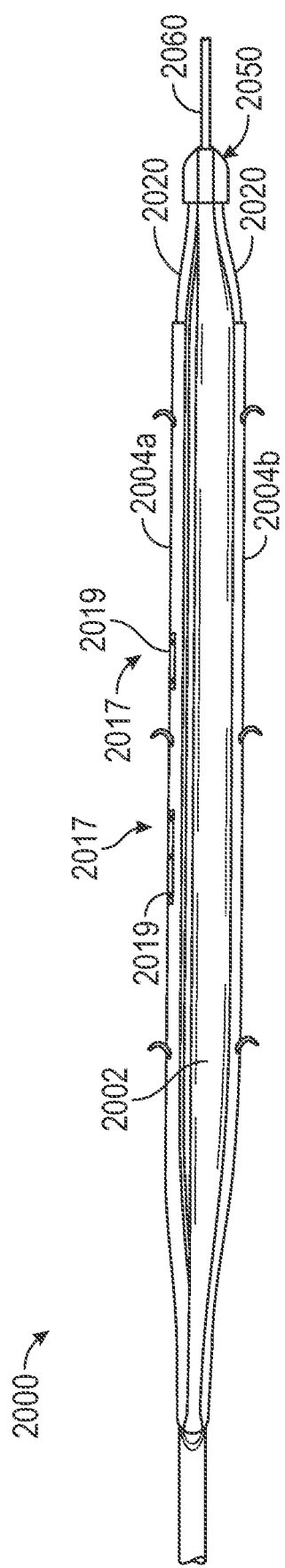
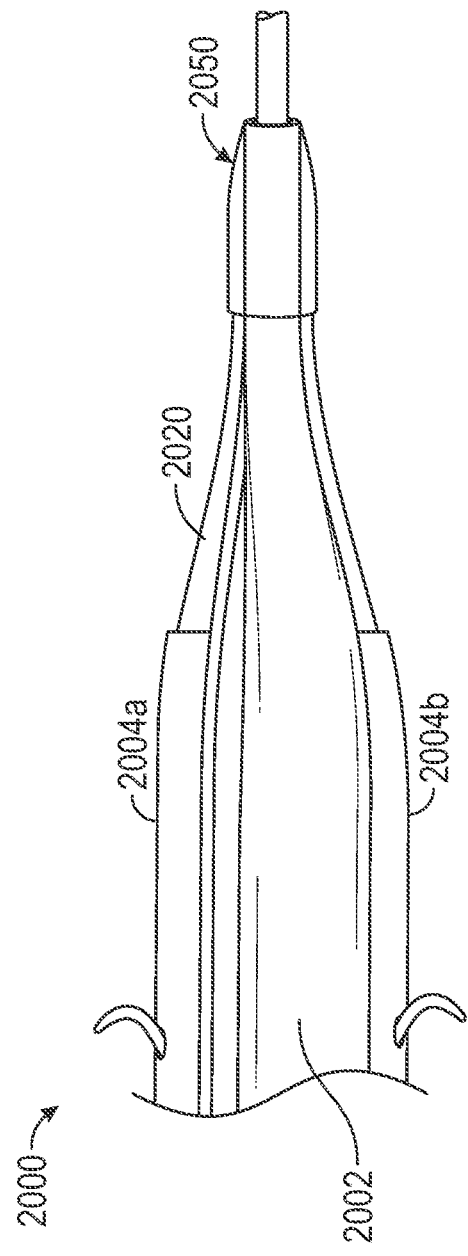
FIG. 20A
FIG. 20B

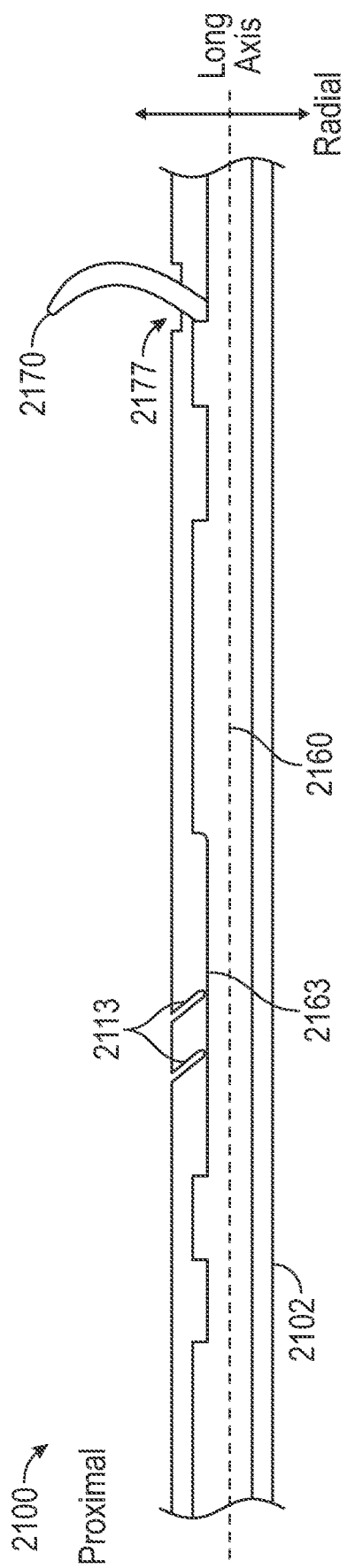
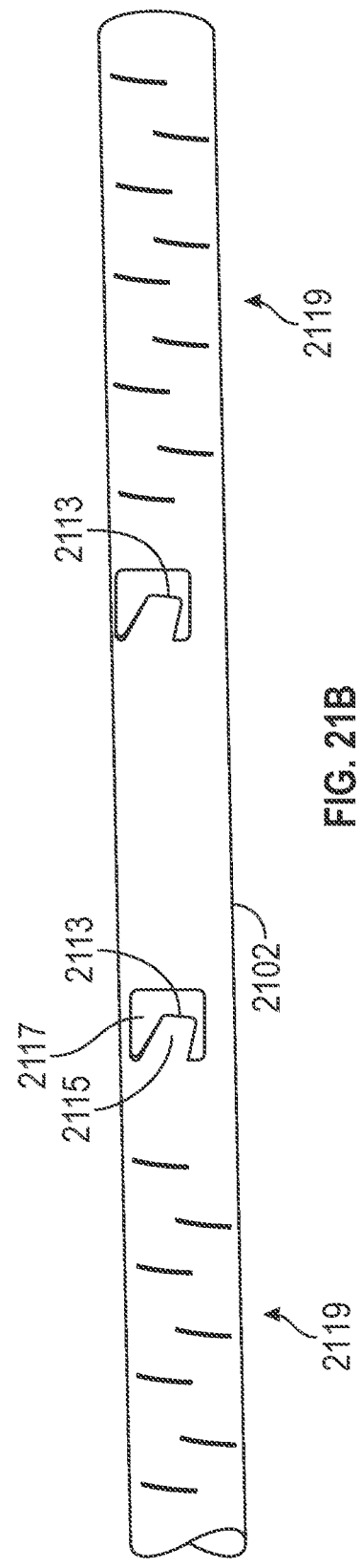
FIG. 21A
FIG. 21B

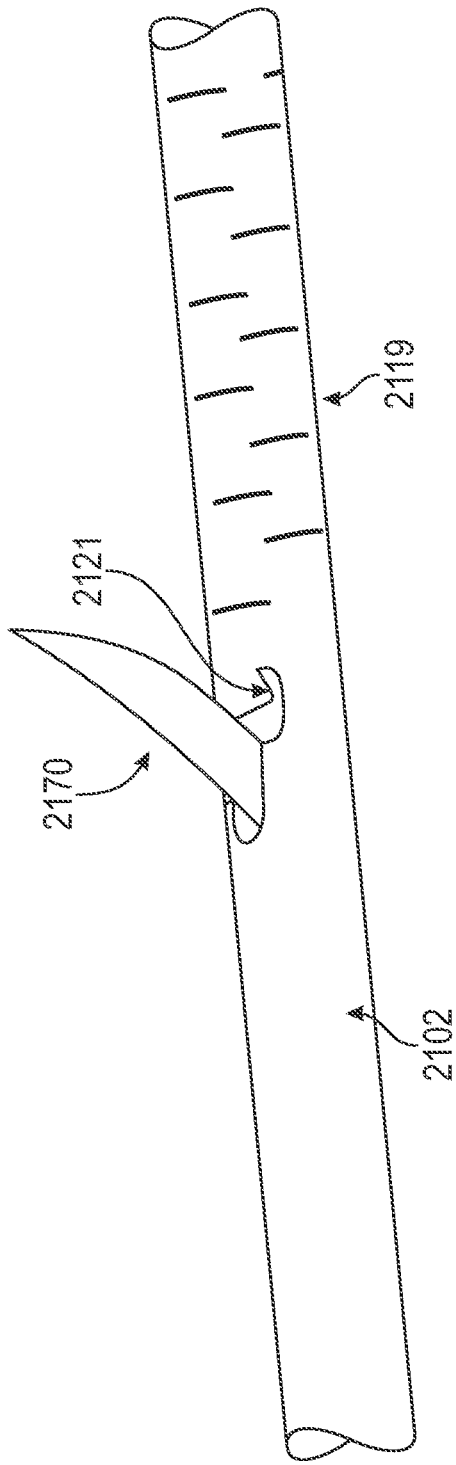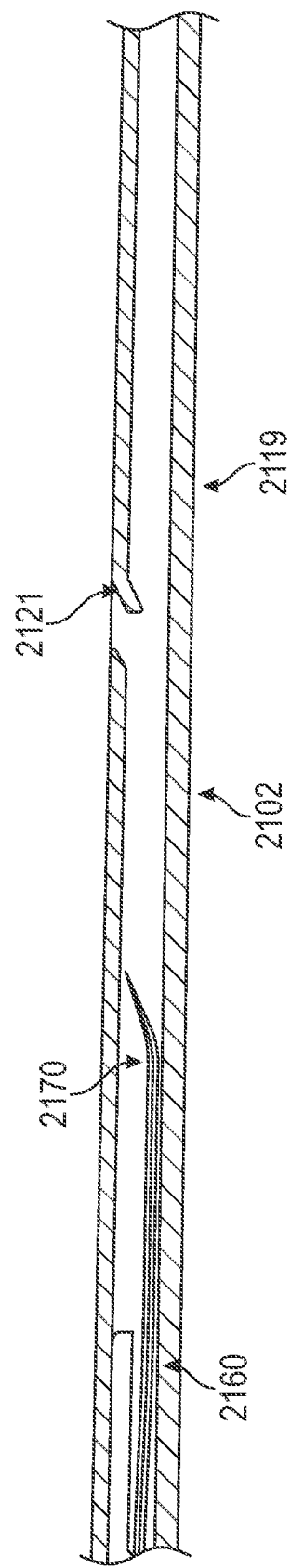

MEDICAL DEVICES FOR FLUID DELIVERY AND METHODS OF USE AND MANUFACTURE

CROSS REFERENCE TO RELATED APPLICATIONS

This application is a continuation of U.S. application Ser. No. 17/937,287, filed Sep. 30, 2022, which is a bypass continuation application of International App. No. PCT/US2022/027049, filed Apr. 29, 2022, which claims priority to U.S. App. No. 63/182,701, filed Apr. 30, 2021, U.S. App. No. 63/202,721, filed Jun. 22, 2021, U.S. App. No. 63/202,933, filed Jun. 30, 2021, U.S. App. No. 63/203,472, filed Jul. 23, 2021, and U.S. App. No. 63/240,812, filed Sep. 3, 2021, the entire disclosures of which are incorporated by reference herein for all purposes.

This application incorporates by reference herein for all purposes the entire disclosures of WO2021/133966, U.S. Pat. No. 11,071,847, issued Jul. 27, 2021, and PCT App. No. PCT/US2022/017068, filed Feb. 18, 2022.

All publications and patent applications mentioned in this specification are herein incorporated by reference to the same extent as if each individual publication or patent application was specifically and individually indicated to be incorporated by reference.

FIELD

Intravascular (e.g., perivascular, adventitial, medial, and/or intimal) delivery of agents for the treatment of peripheral artery disease.

BACKGROUND

It is estimated that more than 20 million patients have peripheral artery disease (PAD), a progressive disease in which plaque (aka lesions or stenosis) builds in the arteries, gradually constricted, reducing and eventually blocking off sufficient blood flow to the lower limbs. Left untreated, PAD can progress to critical limb ischemia (CLI), the most serious form of PAD.

PAD can be treated using a balloon dilatation catheter (angioplasty catheter) to dilate (open-up) the occluded vessel to improve blood flow, yet the vessel tends to reocclude or restenosis over time. Local anti-restenosis drug delivery at the lesion site with drug coated balloons (DCBs) have demonstrated some improvement in patency rates following above-the-knee revascularization, yet DCBs have struggled to demonstrate improved patency following PAD interventions. A variety of causes for inconsistent results from DCB for the treatment of PAD have been proposed by leaders in the field, such as: the high prevalence of intimal and medial calcification in PAD lesions that creates a physical barrier to effective drug penetration into the adventitia of the vessel, resulting in the inability to effectively inhibit a key contributor to the restenosis cascade; limited dosage from smaller drug-coated balloons; and wash-off of the drug from the balloon surface during device delivery to the target lesion site. Some of these same challenges also exist for above-the-knee lesions.

To address these limitations, recent attempts have been made at treating PAD with an infusion catheter following primary angioplasty and/or primary atherectomy intervention. Yet inherent limitations remain with current infusion catheter systems, inclusive but not limited to, the use of a single infusion channel, single needle, and/or a fixed length single needle approach. Due to the limitations of existing infusion catheter systems, treating longer lesions can be time consuming, inherently user dependent, and inconsistent in coverage of the delivered therapy, both circumferentially and longitudinally along the length of the lesion. Furthermore, existing infusion catheter systems lack the added procedural benefit of balloon dilatation, thereby requiring a separate balloon dilatation catheter to be used to dilate the vessel.

Approaches are needed that address one or more of the deficiencies set forth above, including deficiencies of existing scoring balloon catheters to address deep medial calcification that is so prevalent in PAD lesions.

SUMMARY OF THE DISCLOSURE

The disclosure is generally related to balloon dilatation catheters, which are optionally drug-eluting balloon catheters (DEBCs) and to methods for producing and using the same. Any of the DEBCs herein may also be referred to as an apparatus, and any of the apparatuses herein may also be referring to a DEBC.

The balloon dilatation catheters herein are also optionally scoring balloon catheters, which may also be DEBCs.

One aspect of the disclosure is an intravascular apparatus that includes one or more first alignment members and one or more second alignment members, the one or more first alignment members sized, positioned, and configured to interface with the one or more second alignment members to maintain circumferential alignment of needles and spine radial openings to thereby facilitate deployment of the needles out of the spine radial openings.

In this aspect, the apparatus may include rails that each includes one or more first alignment members, and a corresponding spine in which a rail is disposed may include one or more second alignment members.

In this aspect, the intravascular apparatus may additionally include any other suitable feature from the disclosure, such as, without limitation, an inflatable balloon (optionally having an inflated cylindrical configuration), an expandable infusion scaffold comprising one or more spines, and a plurality of movable needle assemblies.

In this aspect, the one or more first alignment members may comprise a rail slot, which may include a flattened rail surface. The one or more second alignment members may comprise one or more spine key members extending radially inward toward a rail slot, wherein the one or more key members may be any of the key members herein. One or more spine key members may be axially spaced from one or more spine sections that have one or more cuts formed therein to increase flexibility.

In this aspect, one or more first alignment members may comprise a rail key member extending radially outward toward the spine.

In this aspect, the one or more spines may include any of the needle deployment guides herein.

An additional aspect of this disclosure is an apparatus that includes one or more spines, the one or more spines including one or more needle deployment guides that extend into a spine lumen and are positioned and configured to guide a needle out of a spine radial opening. In this aspect, the intravascular apparatus may additionally include any other suitable feature from the disclosure, such as, without limitation, an inflatable balloon (optionally having an inflated cylindrical configuration), an expandable infusion scaffold that comprises the one or more spines, and a plurality of movable needle assemblies.

In this aspect, the one or more needle deployment guides may extend radially inward and proximally relative to a spine outer surface.

In this aspect, a portion of the one or more needle deployment guides may be disposed at a distal end of the corresponding spine radial opening, and a second portion of the needle deployment guides may extend radially inward and proximally.

In this aspect, a portion of the one or more needle deployment guides may be disposed at a proximal end of the corresponding spine radial opening, and a second portion of the needle deployment guide may extend radially inward and distally.

In this aspect, the one or more needle deployment guides may comprise a first section that is monolithic with a spine outer surface, and a second section that is not monolithic with the spine outer surface.

In this aspect, the one or more needle deployment guides may extend radially inward at an angle relative to an outermost surface of the spine.

An additional aspect of the disclosure is an apparatus that includes at least one spine securing member that is disposed radially outside of at least a portion of one or more spines, optionally in a location where the one or more spines extend about an outer cylindrical surface of an inflatable member.

In this aspect, the at least one spine securing member may be disposed radially outside of at least a portion of a radially outermost surface of the at least first and second spines. The apparatus may include a plurality of spine securing members, and each of the plurality of spine securing members may be disposed radially outside of at least a portion of a radially outermost surface of one of the at least first and second spines.

In this aspect, the at least one spine securing member may be disposed radially outside of a radially outermost surface of the at least first and second spines along substantially the entire length of the spines, optionally where the spines extend about an outer cylindrical surface of an inflatable member.

In this aspect, the at least one spine securing member may be disposed radially outside of a radially outermost surface of the at least first and second spines where the spines optionally extend about a tapered section of an inflatable member, optionally one or both of a proximal tapered section or a distal tapered section.

In this aspect, the at least one spine securing member may comprise one or more sleeves that are secured to an inflatable member, wherein at least a portion of one of the spines is disposed within a sleeve. The sleeves may circumferentially surround at least a portion of a spine. The one or more sleeves may comprise one or more openings (e.g., radial openings) therein. The one or more sleeves may be bonded to the inflatable member along a radially inner portion of the sleeve and/or to the inflatable member along sides of the sleeve. The one or more sleeves may comprise a first material, and an inflatable member may comprise a second material (optionally the same as or different than the first material), wherein the first material and the second material may facilitate one or more of adhesive or thermal bonding between the sleeve and the inflatable member. First and second materials may optionally comprise a nylon. First and second materials may optionally comprise a polyurethane. Sleeve securing members may include a plurality of openings (e.g., radial openings), each of which may be disposed at the location of one of the spine radial openings. Sleeve securing members may include a plurality of openings, any of which may optionally be disposed at the location of a spine alignment member, such as any of the keys herein.

In this aspect, spine securing members may comprise one or more polymeric materials, such as one or more of a polyimide, a polyurethane, a nylon, or PEBAX®.

In this aspect, the spines securing member(s) may comprise one or more covers that are secured to the inflatable member. A cover may extend radially about at least a portion of all of the spines. A cover may extend radially about a single spine. The one or more covers may include one or more openings (e.g., radial openings).

In this aspect, at least some of the spine securing members (e.g., legs) may be disposed within a distal region of one of the spine lumens, wherein the spine securing members may not extend as far proximally as a distal most needle associated with the corresponding spine. A plurality of spine securing members may or may not be coupled together at their respective distal ends, and may optionally meet each other at a unitary distal end. Distal ends of securing members may be secured in placed by an outer tip member. Spine securing members may extend along a distal tapered region of an inflatable member. Spine securing members may comprise a metallic material such as one or more of nitinol or stainless steel. Spine securing members may include regions that are adapted to expand radially outward as an inflatable member is inflated.

In this aspect, the spine securing members may comprise more than one type of spine securing member.

An additional aspect of the disclosure is an apparatus that includes more than one type of spine securing member.

BRIEF DESCRIPTION OF THE DRAWINGS

FIG. 1 is a side view of a distal region of an exemplary infusion device including an expandable scaffold in an expanded configuration.

FIG. 2A is a side view of a distal region of an exemplary infusion device including an expandable scaffold in an expanded configuration.

FIG. 2B is a side view of a distal region of an exemplary infusion device from FIG. 2A with needles deployed from elongate spines of the scaffold.

FIGS. 6A, 6B, 6C and 6D illustrate views of portions of an exemplary needle sub-assembly or rail track sub-assembly.

FIG. 7A illustrates a top view of an exemplary needle or rail track sub-assembly.

FIG. 7B illustrates a side view of the exemplary needle or rail track sub-assembly from FIG. 7A.

FIGS. 18C and 18D are sectional views of an exemplary apparatus that includes an exemplary securing member that comprises a cover.

FIGS. 19A and 19B are side views of an exemplary apparatus that includes an exemplary securing member that extends within a distal region of a plurality of spines.

FIG. 19C is a sectional view from FIG. 19A.

FIGS. 20A and 20B are side views of an exemplary apparatus that comprises more than one type of spine securing members, including spine sleeves.

FIG. 21A illustrates an exemplary spine that includes alignment members and an exemplary rail that includes an alignment member.

FIG. 21B illustrates an exemplary spine that includes alignment members.

FIG. 21C illustrates an exemplary spine that includes an exemplary needle deployment guide, as well as an exemplary deployed needle.

FIG. 21D illustrates an exemplary spine with a needle deployment guide, and a needle in an undeployed state.

DETAILED DESCRIPTION

Figure 3A:
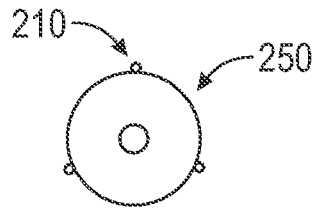
FIG. 3A is an end view of a distal region of an exemplary infusion device with an inflatable member inflated.

The disclosure herein is related to methods, catheters, and systems for the vessel dilatation and optionally delivery of one or more therapeutic and/or diagnostic agents for the treatment of peripheral artery disease. The methods, catheters and systems herein may optionally be adapted to more efficiently and reliably deliver the desired dose of agent to a target region of adventitial tissue, particularly compared to existing drug coated balloons (DCBs) and single-needle infusion delivery devices.

Additionally, the disclosure herein is related to methods, catheters, and systems for the vessel dilatation and delivery of scoring members and deployable needles for the treatment of peripheral artery disease. For clarity, the non-eluting embodiments of the apparatuses are referred to herein as scoring balloon catheters ("SBCs") whereby the microneedles are optionally solid (no inner diameter) and are sized and configured to penetrate and/or crack calcium deep within the vessel wall to further aid in vessel compliance during dilatation. In the SBC embodiments, the infusion lumens that are present in the DEBC embodiment (examples of which are shown in FIGS. 6-10) are eliminated and/or replaced by needle extension members.

It is understood, however, that while DEBCs herein may include what are referred to as infusion spines, the method of using the DEBC may not include the delivery of therapeutic fluid through the needles. For example, DEBC's herein may be used in methods that include vessel dilatation and delivery of scoring members and the application does not necessarily require that fluid be delivered from the needles into the vessel. In these alternatives, the DEBCs may be considered to perform the function of the SBCs herein.

The DEBCs herein may include an infusion scaffold, comprised of one or more infusion spines within which are housed a plurality of deployable needles, which are spaced axially (also referred to herein as longitudinally) and circumferentially apart around the DEBC, allowing more uniform circumferential coverage and a greater span of tissue along the lesion length to be targeted with the agent without having to move the DEBC within the vessel. It is of course understood that any of the treatments herein may include delivering an agent, after which the DEBC may be moved to a different location within the vessel before again delivering the same or a different agent.

Additionally, at least a portion of the DEBC infusion scaffolds herein (e.g., a portion about a cylindrical region of an expanded balloon) may be positioned against a vessel wall upon application of a radially outward force, which is generally described herein as a force applied by an inflatable member or balloon. After the infusion scaffold of the DEBC is apposed against the vessel wall, the needles can be deployed outward such that they pierce through the vessel wall and optionally into the adventitia layer of the vessel wall. Once the needles have been advanced into the wall and optionally into the adventitia, the desired therapeutic agent is delivered though the needles, out of the needles, and into the target tissue within the vessel wall. In some methods, the volume and rate of infusion may be controlled based on one or more of a desired lesion length and/or desired volume of agent infusion.

One or more of any of the following therapeutic agents or types of agents, including but not limited to any combination thereof, may be delivered from the DEBCs herein during any of the methods of use herein: antiplatelet agents; anti-inflammatory agents; antiproliferative drugs as referred to as cell-proliferation inhibitors; immunosuppressants such as mTOR and IMDH inhibitors; anticoagulation drugs; anti-thrombotic agents; lipid-lowering drugs; angiotensin-converting enzyme (ACE) inhibitors; and stem cells. While the disclosure herein focuses on PAD, the device and systems herein may be used to treat alternative conditions, such as, for example only, chronic obstructive pulmonary disease ("COPD"), which is described in U.S. Prov. App. No.

62/953,342, which is incorporated by reference herein in this regard. Agents that may be delivered to treat COPD, for example, include but are not limited to anti-inflammatory agents, receptor antagonists, and neurotoxins.

The disclosure that follows describes non-limiting exemplary DEBCs that are adapted and configured to dilate the intended vessel and deliver one or more therapeutic agents to provide one or more of the advantages set forth herein, such as delivering a desired volume or dose to a target region of tissue in the vessel wall following vessel dilatation for the treatment of PAD.

Figure 5:
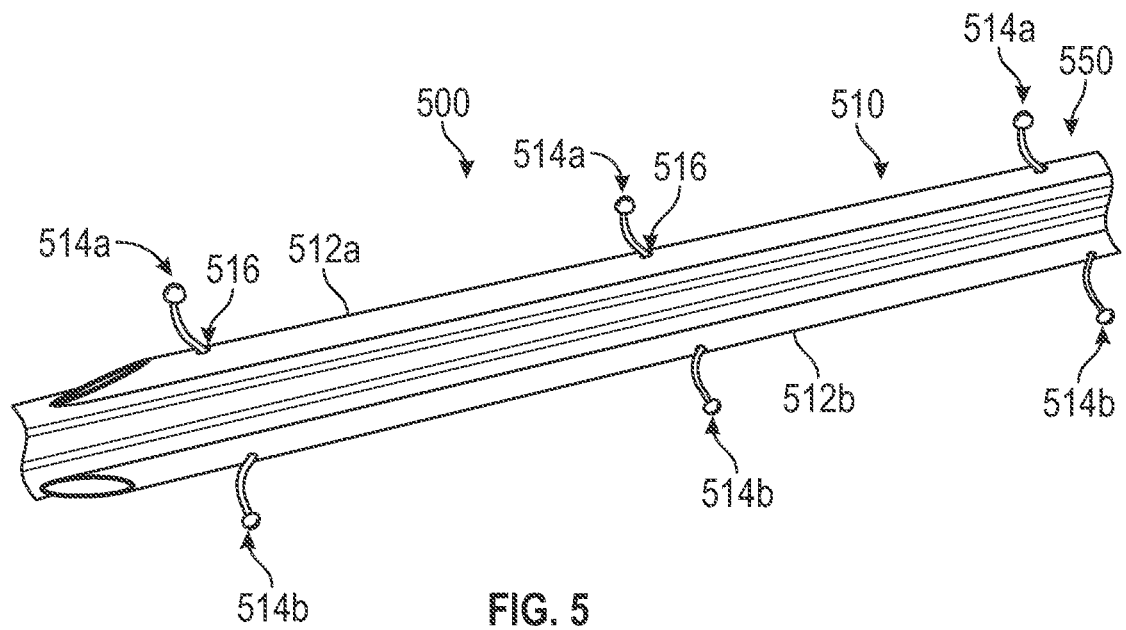
FIG. 5 is a distal region of an exemplary infusion device illustrating needles deployed from spines of an expandable scaffold.

FIG. 1 illustrates a distal region of an example of a DEBC. DEBC 100 includes an expandable infusion scaffold 110 that includes at least first and second infusion spines 112a, 112b, and 112c, from which the needles are not yet deployed. FIG. 5 illustrates an expanded configuration with the infusion needles deployed. Unless indicated herein to the contrary, the infusion spines herein may also be referred to as a plurality of infusion spines. Infusion spines are sized, positioned, and configured to be expandable by a generally radially outward force, which in this example is applied by an inflatable member 150, also referred to as a dilatation balloon. Any of the balloons herein are understood to also be referred to as a dilatation balloon. Any of the inflatable members herein may include one or more of a compliant material (e.g., a polyurethane or a silicone), a non-compliant material (e.g., a polyester or a nylon), or a semi-compliant material (e.g., a nylon). It is understood that some types of materials (e.g., nylon) may be considered to belong into more than one of these categories of material (e.g., non-compliant and semi-compliant), and thus the listing of categories of material herein is not meant to create definite boundaries between the categories of material. Additionally, any of the inflation members herein may be further configured as a drug coated balloon and/or a micro-porous balloon membrane that enables infusion of a therapy through the balloon membrane, which may be used alone or in combination to deliver one or more additional complementary or different agents. A microporous balloon configuration enables the inflatable member to be inflated with a drug solution that is infused through the porous membrane as the balloon is inflated.

As shown, the infusion spines 112a, 112b and 112c are circumferentially spaced about an outer surface of the inflatable member 150 with a long axis (LA) of the DEBC when the spines are expanded. The long axis in this embodiment is also a long axis of the inflatable member 150. In this example, the spines are parallel (or substantially parallel) with the long axis of the DEBC 100 and the inflatable member 150 when expanded, as shown. As used herein, the phrase substantially parallel in this context includes slight deviations from being parallel and includes spines that have configurations that still facilitate the efficient and effective delivery of therapeutic agent to the desired tissue. One of skill in the art will appreciate that substantially parallel as used in this context allows for some deviation from strictly parallel, such as at an angle of five or ten degrees relative to a long axis, for example.

Figure 23A:
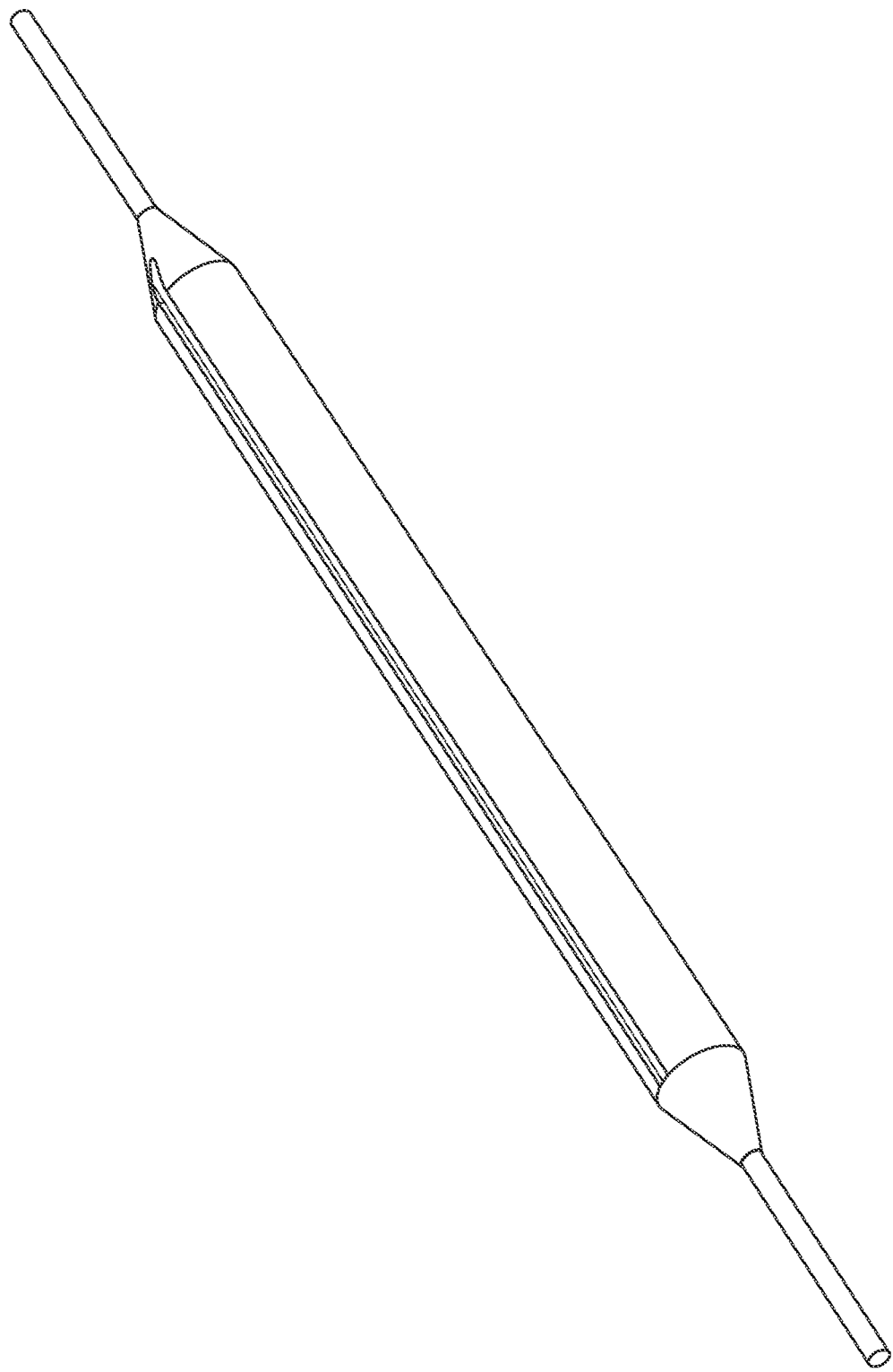
FIGS. 23A and 23B illustrate an exemplary inflatable member.
Figure 23B:
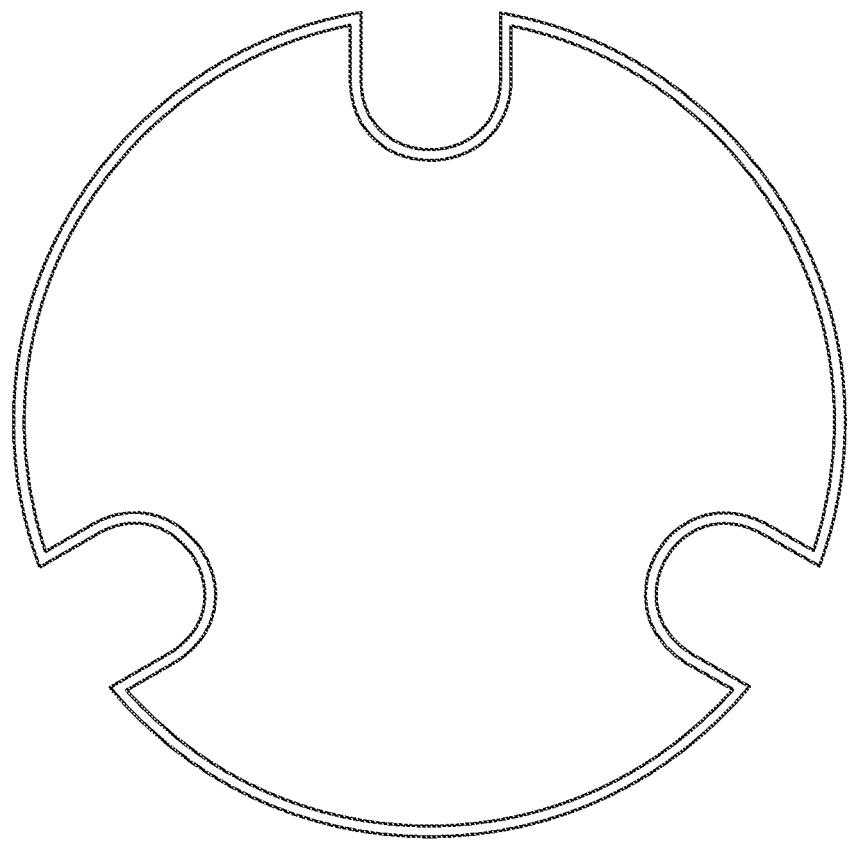

In this example the inflatable member has a cylindrical configuration when expanded, as shown. The term cylindrical as used in this context includes configurations that approximate a cylinder even if not perfectly cylindrical, which may be the case if a plurality of infusion spines are secured to (including indirectly), attached to or engaging an outer surface of the inflatable member and the balloon does not have a perfectly cylindrical configuration when expanded. FIGS. 23A and 23B illustrate an exemplary dilatation balloon having a cylindrical configuration when expanded even though it is not perfectly cylindrical. For example, FIGS. 23A and 23B illustrate a dilatation balloon with a cylindrical configuration that has a plurality of axially-extending grooves, indentations, or depressions in the expanded configuration, as shown. Axially-extending grooves herein need not be purely longitudinally arranged, but may have other arrangements such as being helically arranged along the length of the dilatation balloon. Additionally, an inflatable member may still be considered to have a cylindrical configuration even if the inflatable member has at least one end region that is tapered or has any other configuration that is not orthogonal with the long axis, such as the tapered distal and proximal ends of the inflatable member that are shown in FIG. 1. Additionally, for example, an inflatable member with a general dumbbell configuration may be considered to have a cylindrical configuration. Additionally still, when the description herein describes inflatable members having cylindrical configurations when expanded, it refers to the configuration the inflatable member would take after being expanded outside of a patient. This is meant to clarify that when expanded or inflated within a vessel of the patient, there may be one or more anatomical restrictions that prevent the inflatable member from transitioning to the cylindrical configuration it would assume if expanded outside of a patient, such as the configuration of the vessel wall in which the DEBC is placed. In both scenarios, the inflatable member in these examples is considered to have a cylindrical or somewhat cylindrical configuration when expanded.

The infusion spines herein may be connected (directly or indirectly) to the inflatable member, such as by one or more of bonding, adhesion, laser welding, an outer cover, an outer sleeve, or using any other suitable technique for securing the spines to an inflatable member, such as any of the securing members herein, which are described in detail below.

Figure 11A:
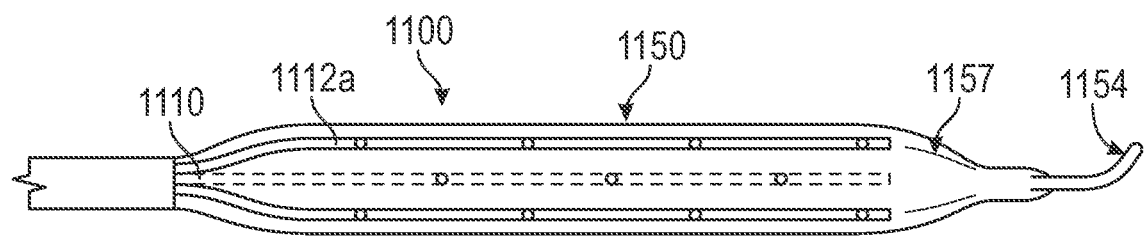
FIG. 11A illustrates a side view of an exemplary infusion device in a collapsed lower profile delivery configuration.
Figure 11B:
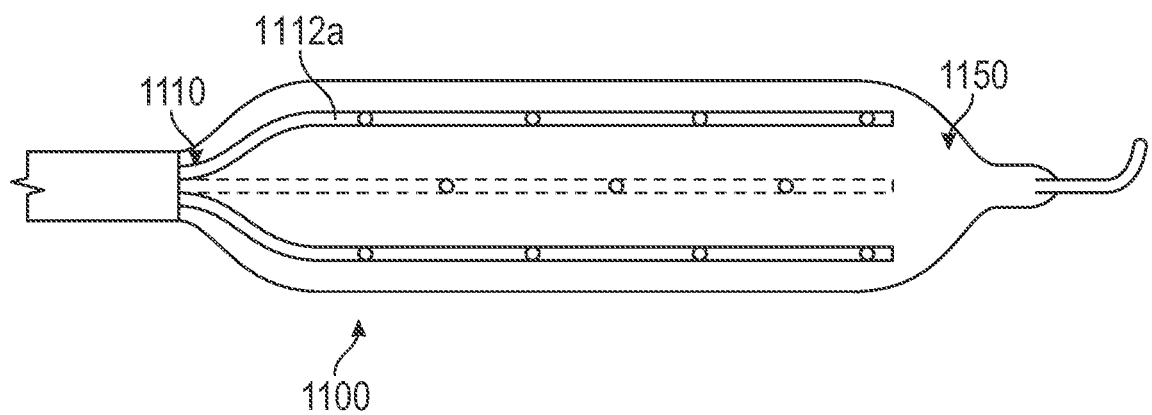
FIGS. 11B and 11C illustrate side and end views, respectively, of the exemplary infusion device from FIG. 11A in an expanded configuration with needles deployed.
Figure 11C:
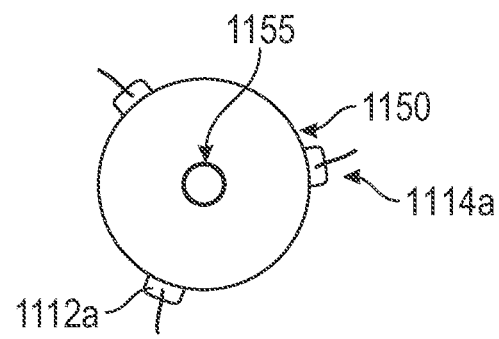

FIG. 1 shows an exemplary inflatable member 150 and an expandable infusion scaffold 110, both in an expanded state or configuration. For delivery, the expandable infusion scaffold is in a collapsed delivery configuration in which the infusion spines are closer to adjacent spines than in the expanded state, such as shown in FIG. 11A. It is understood that FIGS. 11A-11C are an alternative embodiment, and the reference to FIG. 11A is meant to illustrate an infusion scaffold in a collapsed delivery configuration (or at least a configuration in which it is not fully expanded). During delivery, the inflatable member is also in a lower profile unexpanded (and uninflated) collapsed delivery configuration. The internal volume of the inflatable member is also less in the delivery state than in the deployed state. Once the DEBC is delivered to the target location with a vessel, the inflatable member is inflated, which pressurizes the inflatable member. This expansion of the inflatable member causes the inflatable member to increase in a radial dimension and apply a force to the plurality of infusion spines that are disposed around the inflatable member. This causes the spines to expand radially and which also causes the relative circumferential distance between the spines to increase, an example of which is shown in FIG. 11B. The expandable infusion scaffold is thus expanded towards the vessel wall by inflating and expanding the inflatable member.

The inflatable member may have a variety of collapsed states or configurations. For example, the inflatable member may be folded in one or more locations to facilitate its collapse, while in other embodiments the inflatable member may not have a particular or well-defined collapsed state.

The inflatable members herein are sized and configured such that when expanded, the plurality of infusion spines will be moved radially outward and in contact or substantial contact with the vessel wall, or an optional cover or sleeve disposed radially about the spine(s) may contact the vessel wall. If the disclosure herein refers to one or more spines contacting a vessel wall, it is understood that if the apparatus includes one or more optional securing members (e.g., covers or sleeves) radially about the spine, the securing members may make direct contact with the vessel wall. It is understood that due to some variability in vessel wall size and the shape of the balloon, some portion of any of the infusion spines (or cover(s)/sleeve(s)) may not make direct contact with vessel wall. The inflatable member may be sized such that it may have a deployed diameter that is larger than an intended vessel size to help ensure that the infusion spines (or optional cover(s)/sleeve(s)) are in contact or substantial contact with the vessel wall. Maintaining sufficient pressure in the inflatable member such that the infusion spines are in substantial contact with the vessel wall can help support the needles as they are deployed and pierce through the vessel wall, which is described in more detail below.

Any of the expandable scaffolds herein may have infusion spines that are optionally equidistantly spaced apart along their lengths, an example of which is shown in FIG. 1. For example, two infusion spines may be spaced apart 180 degrees around the inflatable member when the scaffold and infusion spines are expanded. Alternatively, three infusion spines may be spaced apart 120 degrees around the inflatable member when the scaffold and infusion spines are expanded. Alternatively, four infusion spines may be spaced apart 90 degrees around the inflatable member when the infusion spines are expanded, and so forth. In the collapsed delivery state, the infusion spines of the scaffold can also have the same general relative relationship even though they are closer together and not spaced as far apart.

While equal spacing between spines may in some applications provide more complete delivery of the agent to the target tissue around the vessel wall, in alternative examples the infusion spines may not all be equidistantly spaced apart around the inflatable member.

Figure 16:
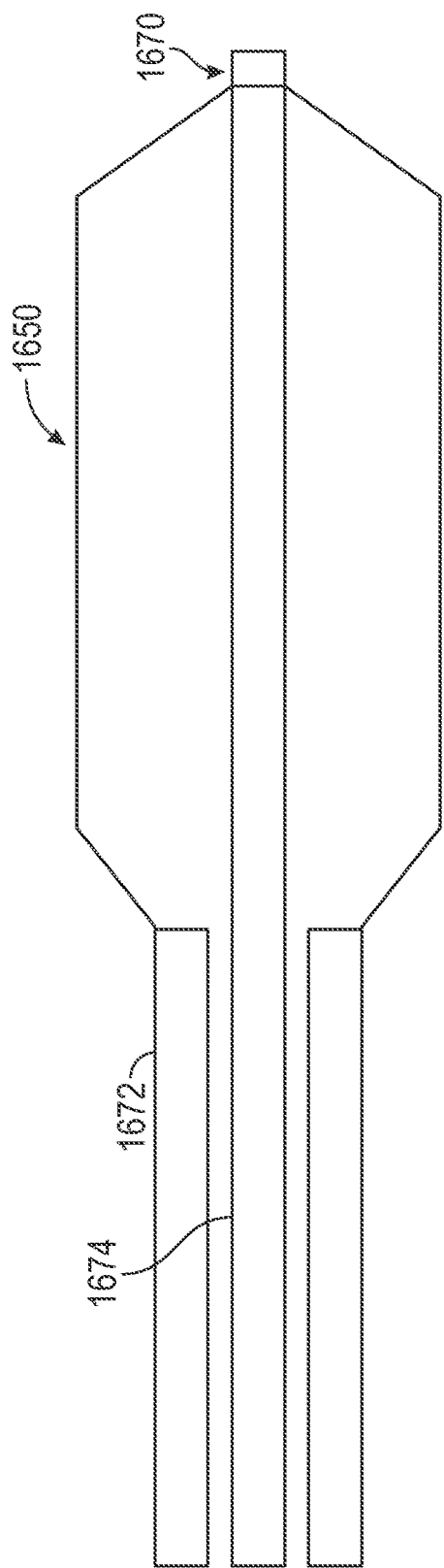
FIG. 16 is a side view illustrating an exemplary manner in which an inflatable member may be secured to a catheter shaft.

FIG. 16 illustrates a distal portion of an exemplary DEBC, wherein the expandable scaffold is not shown for clarity. In this example, the DEBC includes an inflatable member 1650, which is shown inflated. A distal end of inflatable member 1650 is coupled to inner shaft or member 1670, and a proximal end of inflatable member 1650 is coupled to outer shaft 1672. The inner and outer shafts 1670 and 1672 define therebetween inflation fluid pathway 1674, which is in fluid communication with an interior volume of inflatable member 1650. The inner volume of inflatable member 1650 and fluid pathway 1674 are in fluid communication with a fluid inflation port, such as inflation port 1333 or inflation port 1433 shown in FIGS. 13 and 14, and which are described in more detail below. Alternatively, the inflatable members herein may be secured to the DEBC in a manner that may be the same or similar to known balloon angioplasty catheters, examples of which are described in U.S. Pat. No. 4,782,834 and U.S. Ser. No. 10/086,175, and which are incorporated by reference herein for all purposes.

Once the expandable inflation scaffold is expanded and in contact with (or at least substantially in contact with) or directly adjacent the vessel wall, each of a plurality of needles are deployed outward from a radial opening in the infusion spine, an example of which is labeled in FIG. 5 as opening 516. FIG. 1 illustrates a plurality of needles deployed from the expandable infusion scaffold, and in this example shows a plurality of needles deployed from each of the infusion spines. Needles 114a are shown deployed from infusion spine 112a. Needles 114b are shown deployed from infusion spines 112b. Needles 114c are shown deployed from infusion spines 112c. In this merely illustrative example, there are three needles shown deployed from each of the infusion spines. In any of the embodiments herein, each infusion spine may be associated with from two to fifty needles, all of which can be deployed from a radial opening in the spine. As used in this context, the terms associated or corresponding refer to needles that are within any particular spine in an undeployed state, and are deployable from that particular spine to pierce the vessel wall.

When this disclosure refers to an infusion spine, it is generally referring to one of the infusion spines of the expandable scaffold. Additionally, when a feature is described with respect to any particular or individual infusion spine, it is understood that all of the infusion spines of any particular scaffold may also have any or all of those features. The phrase infusion spine herein may be used interchangeably with the term spine.

The needles in any infusion spine herein are generally axially spaced apart, as shown in the examples of FIGS. 1, 2B and 5, for example. Spacing the needles axially apart can provide maximum coverage of the therapeutic agent along the length of the target lesion, which can increase the volume of tissue that may be targeted by using the DEBCs herein. Additionally, by having a plurality of infusion spines spaced around or about the device, with each infusion spine having a plurality of axially-spaced needles deployable therefrom, the DEBCs herein can ensure or increase the likelihood of delivering the agent to as much target tissue around the vessel as possible without having to rotate or move the DEBC to provide the desired circumferential coverage of the infused agent. It is of course understood that the DEBCs herein may also be moved in between episodes of agent delivery into the vessel wall. In these instances, the needles may be retracted, and the DEBC can be moved to a different location within the vessel or to a different vessel. The inflatable member and the scaffold are generally collapsed (at least partially) before moving the DEBC to a new location.

In any the DEBCs herein, any two axially spaced needles associated with an infusion spine may be spaced from 1 mm to 40 mm apart, such as from 5 mm to 35 mm apart, such as from 10 mm to 30 mm apart, such as from 15 mm to 20 mm apart.

In any of the DEBCs herein, any adjacent pair of three or more needles that are associated with a single infusion spine may be equidistantly spaced apart axially. Alternatively, any adjacent pair of three or more needles associated with a single infusion spine may not be equidistantly spaced apart axially. It is of course understood that any spine herein may only be associated with two needles, and this paragraph is only related to spines that may be associated with more than two needles.

In some illustrative embodiments, any of the DEBCs herein may include from six to 50 needles total. For example, an DEBC with three spines, each associated with two needles, would have six needles total.

FIG. 1 illustrates an example in which the infusion spines do not have the same lengths and do not have distal ends that extend as far distally as at least one other distal end. In this example, the lengths of all of the spines that are shown are different, and none of their distal ends are axially aligned. In any of the DEBCs herein, any of the spines may have lengths that are the same such that their distal ends are axially aligned with any other spine distal end. In this context, the term length generally refers to the portion of the spine that overlaps with the inflatable member rather than a portion of a spine that may also extend proximally from the inflatable member.

The needles in different spines may or may not be axially aligned. For example, the exemplary needle placement in FIG. 1 shows none of the needles being axially aligned with needles in circumferentially adjacent spines. Any of the needles in the different infusion spines, however, may be axially aligned. Likewise, the infusion spines may also be axially aligned. For example, the DEBC may have rows of needles, with the rows spaced apart axially along the length of the DEBC, an example of which is shown in FIG. 5. A row as used in this context refers to two or more needles in different spines that are axially aligned. The apertures in the top and bottom spines in FIG. 11B are axially aligned, which will cause the needles associated with the top and bottom spines in FIG. 11B to be axially aligned when deployed.

In any of the DEBCs herein, the number of needles associated with each of the infusion spines is the same. FIG. 1 shows an example of this, with three needles per infusion spine. In alternatives, the number of needles in each of the infusion spines may not be the same. For example, one spine may be associated with two needles, while a second spine may be associated with three needles. Any of the DEBCs herein may have an expandable scaffold with a plurality of spines, optionally wherein none of the spines has the same number of needles as any other spine.

Figure 4A:
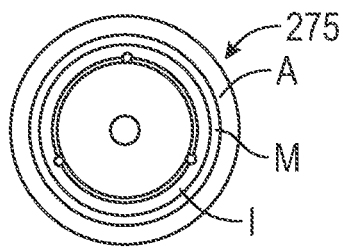
FIG. 4A is an end view of a distal region of the exemplary infusion device from FIG. 3A, shown within an exemplary vessel.
Figure 3B:
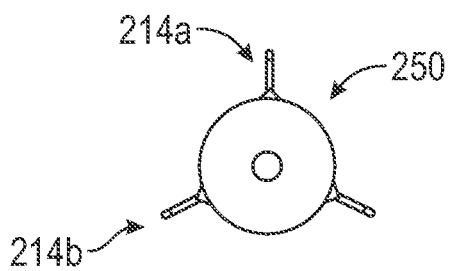
FIG. 3B is an end view of a distal region of the exemplary infusion device in FIG. 3A, shown with needles deployed.
Figure 4B:
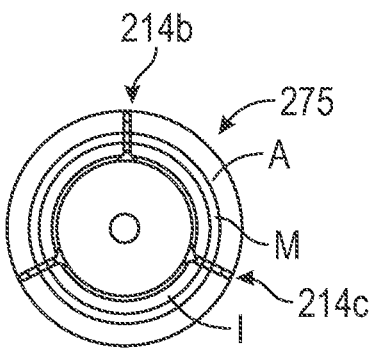
FIG. 4B is an end view of a distal region of the exemplary infusion device in FIG. 3A shown with needles deployed and within an exemplary vessel.

FIGS. 2A, 2B, 3A, 3B, 4A and 4B illustrate an exemplary DEBC 200 with an expandable infusion scaffold 210 that includes a plurality of infusion spines 212 (one labeled as 212a). Any suitable feature from FIG. 1 or described elsewhere herein may be incorporated into DEBC 200. DEBC 200 also includes inflatable member 250 that when inflated and expanded causes the expandable infusion scaffold 210 to expand, described in more detail elsewhere herein. Each of the plurality of infusion spines includes a plurality of radial openings or windows 216 (shown in FIG. 2A), through which the plurality of needles 214 (labeled as 214a, 214b and 214c for the different spines) extend when deployed. FIGS. 2A (side view), 3A (end view) and 4A (end view in an exemplary vessel 275) show the DEBC after the inflatable member 250 has been inflated but with the needles not yet deployed, while FIGS. 2B, 3B and 4B show exemplary needles 214 deployed through the openings in the infusion spines 212. FIG. 4B illustrates the needles 214 piercing through the vessel wall 275 and extending into the adventitia "A." FIGS. 4A and 4B illustrate intimal "I," medial "M," and adventitial "A" layers of the vessel. Any other disclosure herein from any other example may be incorporated into the examples in FIGS. 2A-4B.

Generally, the infusion spines herein include a lumen and a plurality of openings or windows therein, such as openings 216 in FIG. 2A. The needles herein are generally disposed within an infusion spine in a delivery state and are deployed from the infusion spine out of one of the needle openings to pierce the vessel wall. The needles herein may be disposed within and deployed from the infusion spines in a variety of ways. Additionally, the needles herein may be in fluid communication with a fluid source in a variety of ways. The examples below are meant to be illustrative. The needles herein associated with an infusion spine may be deployable at the same time. The needles herein associated with an infusion spine may be deployable by moving them together as a unit, such as if they are coupled to a common axially movable member within the spine. The needles herein associated with an infusion spine may be separately deployable from within the spine.

Each of the plurality of needles associated with an infusion spine may be coupled to an axially moveable member that is disposed within the infusion spine, such that axial movement of the axially moveable member relative to the infusion spine causes the axial movement of the needle relative to the infusion spine.

In some embodiments herein, the needles associated with an infusion spine are adapted to be moved together in unison upon the axial movement of an axially movable member, which may be referred to in this context as a common axially moveable member. In some alternatives, the needles associated with an infusion lumen may be axially moved independently from one another, such as when each needle is coupled to its own or individual axially moveable member within the spine.

In some embodiments the axially moveable member (which may be referred to as a rail track) is a separate structure that does not specifically define a fluid lumen, although in these examples the axially moveable member may house therein one of more fluid lumens that are in fluid communication with one or more needles. Additionally, in these embodiments, one or more fluid lumens within the axially movable member may also be moved axially relative to the infusion spine in response to axial movement of the axially moveable member.

FIG. 5 illustrates an exemplary DEBC 500, which may incorporate any of the disclosure related to DEBC 100 shown in FIG. 1 or any other feature described herein. DEBC 500 includes an expandable infusion scaffold 510, which includes a plurality of infusion spines 512a, 512b (a third infusion spine 512c is not visible in the side view of FIG. 5). The infusion spines 512a and 512b each include a plurality of openings 516 through which the needles are deployed. In this example, each of the spines is associated with three needles as shown, but more or fewer may be associated with each infusion spine as is described elsewhere herein.

Figure 6E:
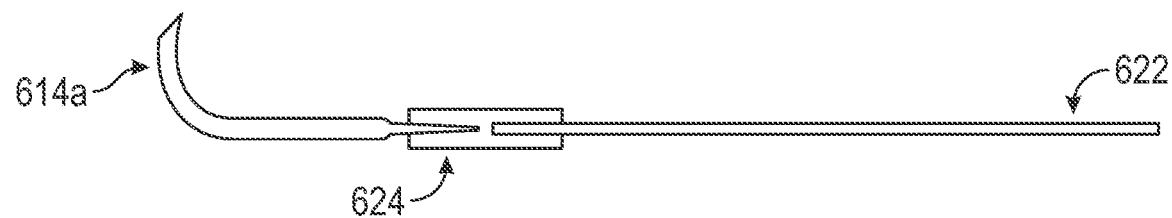
FIG. 6E illustrates an exemplary needle secured to a fluid delivery lumen.
Figure 6F:
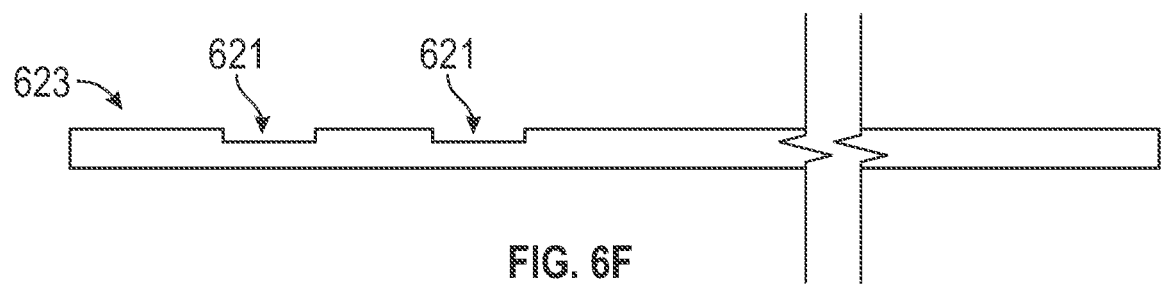
FIG. 6F illustrates an exemplary rail.
Figure 6G:
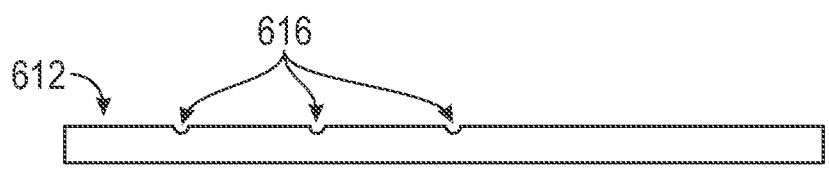
FIG. 6G illustrates a portion of an exemplary infusion spine.

FIGS. 6A-6F illustrates exemplary features of an exemplary needle subassembly 620 (any of which may be referred to herein as a rail track subassembly, and vice versa), with the infusion spine not shown for clarity. Rail track subassembly 620 is configured to both move the needles to deploy them from the infusion spine openings, as well as provide housing for one or more fluid lumens that are in fluid communication with one or more needles, and such fluid communication to the needles to deliver the agent into the vessel wall when the needles are deployed from the openings in the infusion spine. FIG. 6E illustrates an exemplary needle 614a coupled to fluid lumen 622 with an optional coupler 624. In other embodiments any of the needles herein may be directly connected to a fluid lumen. The needle 614a and fluid lumen 622, as shown in FIG. 6E, are then positioned within rail 623, which is shown alone in FIG. 6F. Rail 623 is an example of an axially movable member that is configured to be axially moved to cause the axial movement of a plurality of needles. Rail 623 is also sized and configured to house therein one or more fluid lumens, in this case fluid lumen 622" and fluid lumen 622''', as shown in FIG. 6D. As shown in FIG. 6D, in this example each needle is in fluid communication with a distinct or individual fluid lumen, but they are coupled to rail 623 such that they move axially together in unison when rail 623 is moved. With respect to FIG. 6E, each needle is coupled to an individual fluid lumen as shown, then advanced through rail 623 and coupled thereto, as is shown in FIGS. 6A-6D. FIG. 6D illustrates one example of a plurality of individual fluid lumens 622" and 622''' housed or disposed within a lumen of rail 623. Rail 623, at least in this exemplary embodiment, can be moved axially to axially move all of the needles, as well as serve to house the individual fluid lumens therein.

The needle subassembly 623 shown in FIG. 6A can be then positioned in one of the infusion spines, such as by front loading or back loading. When the needle subassembly 620 is loaded into an infusion spine, the needles will deflect radially inward towards the openings 621 that are labeled in FIG. 6F, and the needle subassembly may be positioned in the infusion spine such that the needles are just proximal to the infusion spine openings 616, labeled in the exemplary spine 612 shown in FIG. 6G.

Any of the needles herein may be formed with a natural bias towards a deployed configuration in which the needles extend at least partially radially outward, such as is shown in FIGS. 6A, 6B, 6C, 6D and 6E. When the needles are collapsed radially down or inward for delivery, they may or may not have a perfectly linear configuration due to their naturally biased and curved deployed configuration. When collapsed for delivery, any of the needles may retain a slight curvature in their configuration.

The use of the term rail herein does not necessarily impart any structural limitations. The rails herein may be elongate members that are sized and adapted to be moveable within an infusion lumen to facilitate the movement of one or more needles. Any of the rails herein may be a tubular member or partial tubular member, such as rail 623 shown in FIGS. 6A-6F, or any other elongate member (with or without a lumen) that is sized and configured for axial movement within a spine.

As part of an exemplary manufacturing of a rail track assembly, the needle and corresponding fluid lumen may be front-loaded through the rail. A coupler (e.g., 624" or 624'''), if used, may be secured (e.g., bonded, welded, or otherwise secured thereto) to the needle and fluid lumen as shown in FIG. 6E. The rail openings 621 may be formed by removing sections of the material of rail 623, which may itself be an elongate tubular member, such as a stainless steel or nitinol tubular member.

Each infusion spine in the exemplary DEBC shown in FIGS. 6A-6F is associated with at least three subcomponents or subassemblies—the infusion needle(s), the infusion lumen(s), and the rail track subassembly housing the respective infusion needle(s) and infusion lumen(s).

In any of the examples herein, any of the fluid delivery lumens may have an inner diameter from 0.001 inches to 0.025 inches, for example. Fluid delivery lumens herein may also be referred to herein as fluid lumens.

In any of the examples herein, any of the axially moveable members (such as any of the rails) may have an outer diameter from 0.005 inches to 0.10 inches.

In any of the examples herein, any of the axially moveable members may have openings (e.g., openings 621) that are axially spaced from 2 mm to 80 mm apart, such as from 10 mm to 50 mm.

In any of the examples herein, any of the axially moveable members may have openings (e.g., openings 621) that have a length from 0.5 mm to 20 mm.

In any of the examples herein, any of the spines may have an outer diameter from 0.01 inches to 0.20 inches.

In any of the examples herein, any of the spines may have openings (e.g., openings 216, 516) that are axially spaced apart from 2 mm to 80 mm.

In any of the examples herein, any of the spines may have openings (e.g., openings 216, 516) with a width or length dimension from 0.05 mm to 10 mm.

FIGS. 7A and 7B, in top and side views, respectively, illustrate an exemplary rail track subassembly 720 (spine not shown for clarity), with three exemplary needles in deployed configurations. Any of the features from assembly 620 of FIG. 6A may be incorporated into assembly 720. Rail track subassembly 720 includes rail 723, which has openings 721 therethrough (only one of which is labeled in FIG. 7A), and in this example there are three openings 721 in rail 723. Needles 714a are coupled to individual and distinct fluid lumens 722, optionally via couplers 724 but alternatively directed connected thereto, which may be secured to rail 723 to secure the needle to the rail 723 and provide unitary axial movement of the needles 714 (which are individually labeled as 714a', 714a", and 714a''').

FIGS. 7A and 7B also illustrate how fluid lumens may extend through the rail 723 lumen. For example, fluid delivery lumen 722' is in fluid communication with needle 714a' and extends through rail 723. Fluid delivery lumen 722' extends adjacent to central needle 714a" and fluid delivery lumen 722", as shown in the central regions of FIGS. 7A and 7B. In the proximal region shown in FIGS. 7A and 7B, all three fluid delivery lumens 722', 722" and 722''' are adjacent one another within the rail 723. Any of the fluid delivery lumens herein may include a bend or deviation in its path such that it can pass next to a different needle and its associated fluid delivery lumen, which is shown in FIGS. 7A and 7B. In this manner, the needles can extend in the same direction from the spine, which can be seen in the top view of FIG. 7A. In the top view of FIG. 7A, the needles are all extending upward, or out of the page.

Figure 8:
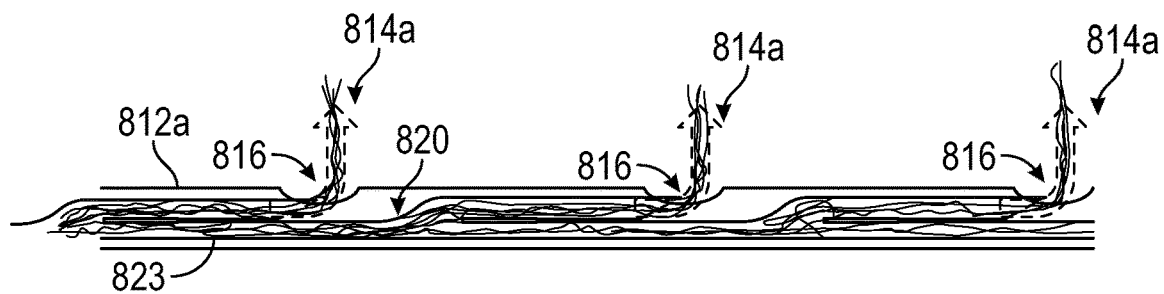
FIG. 8 is a side view of a plurality of exemplary needles deployed outward from an infusion spine.

In some embodiments, the axially movable member may also define a fluid lumen that is in fluid communication with one or more needles, such as in the example shown in FIG. 8. FIG. 8 illustrates an exemplary needle assembly 820 shown within an exemplary spine 812a, which includes top or radially outward openings 816. Needle assembly 820 is an axially movable member that in this embodiment also defines a fluid delivery lumen as shown that is in fluid communication with all of the needles 814a. Needles 814a are shown in their deployed configuration (tissue not shown for clarity) extending out of the spine openings 816. Any other feature from any other example herein may be incorporated into the features shown in FIG. 8, including use with any other inflatable member herein.

Any of the lumens herein (e.g., infusion spine lumen, rail lumen, and/or fluid lumen) may have or benefit from having one or more regions with sufficient flexibility to allow for the DEBC to be delivered to the target location in the vasculature. For example, any of the lumens herein may incorporate a tubular member with one or more regions with one or more cuts therein (e.g., a laser cut or other technique) that imparts some degree of flexibility along at least a portion of its length. Cuts made in any tubular member herein may be in the form of, for example without limitation, including combinations thereof, an at least partial spiral pattern, an at least partial brick pattern, or any other pattern that increases the flexibility of the infusion lumen (an additional example of which is shown in a spine in FIGS. 21B and 21C, which includes linear cuts that do not extend 360 degrees around the circumference of the spine). More than one pattern may be implemented in any lumen (spine lumen, rail lumen, fluid delivery lumen, etc.), and the shape or configuration of a cut pattern may change along the length of the lumen.

Any of the fluid lumens herein may optionally include a non-permeable membrane on one or both of an inside or the outside, such as an elastomeric membrane (e.g., urethane, silicone, or hydrogel), which can prevent fluid from leaking therethrough. For example, any lumens that may include or more cuts therein (e.g., laser cut tubes) may include one or more membranes secured thereto to maintain fluid integrity.

Any of the lumens herein may comprise, for example, any combination of nitinol, stainless steel, polymer tubing, polyimide, braided tubing, or other structural material. Any of the lumens herein may be constructed to provide the desired fluid integrity and/or flexibility when being delivered to the target delivery site.

Figure 12:
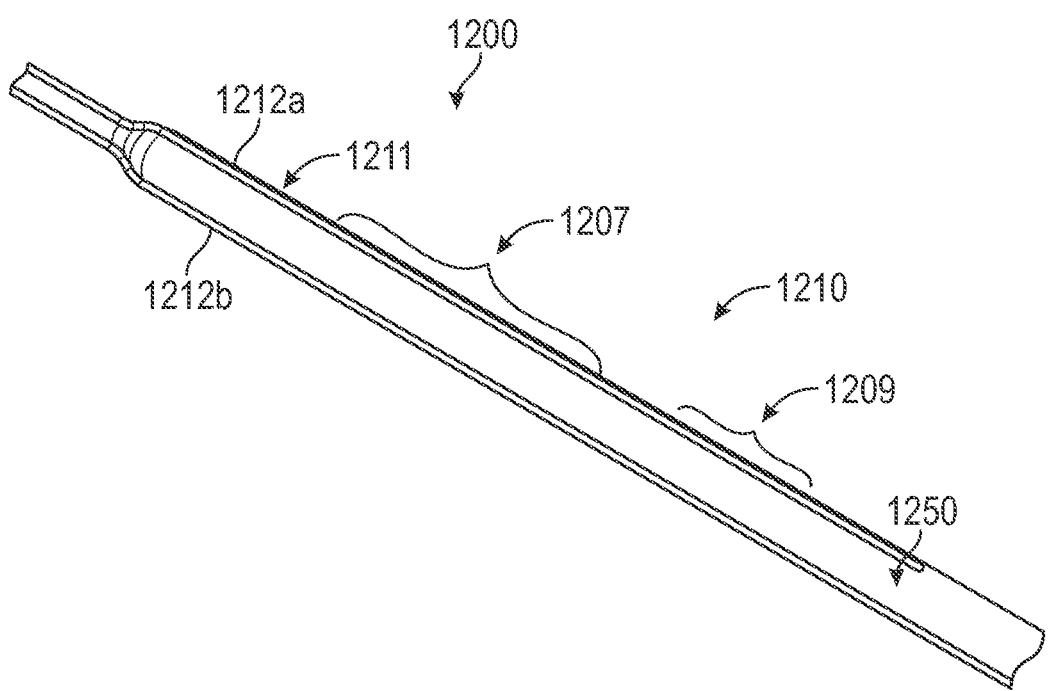
FIG. 12 illustrates a distal region of an exemplary infusion device in an expanded configuration, with regions that are more flexible than other sections of the spine.

In some examples, sections of the infusion spine(s) in between needle regions may be more flexible to provide more flexibility at those locations, while the spine regions where the needles are deployed may have relatively higher stiffness to aid the needle piercing through tissue or calcifications. FIG. 12 illustrates an exemplary infusion device 1200, with inflatable member 1250 and scaffold 1210 in expanded configurations or states. Scaffold 1210 includes a plurality of spines 1212a and 1212b. Spine region 1207 may be configured to be more flexible than distal region 1209 and proximal region 1211 that are axially adjacent to region 1207. Needles may be present in regions 1209 and 1211, for example. Each spine may have a plurality of regions 1207 that are more flexible that other sections of the spine, any of which may be axially spaced apart with less flexible spine regions in between, which is described in more details with respect to FIG. 13. As set forth herein, spine 2102 shown in FIG. 21B includes exemplary axially spaced apart regions 2119 that include cuts therein to impart flexibility in those regions 2119.

Figure 13:
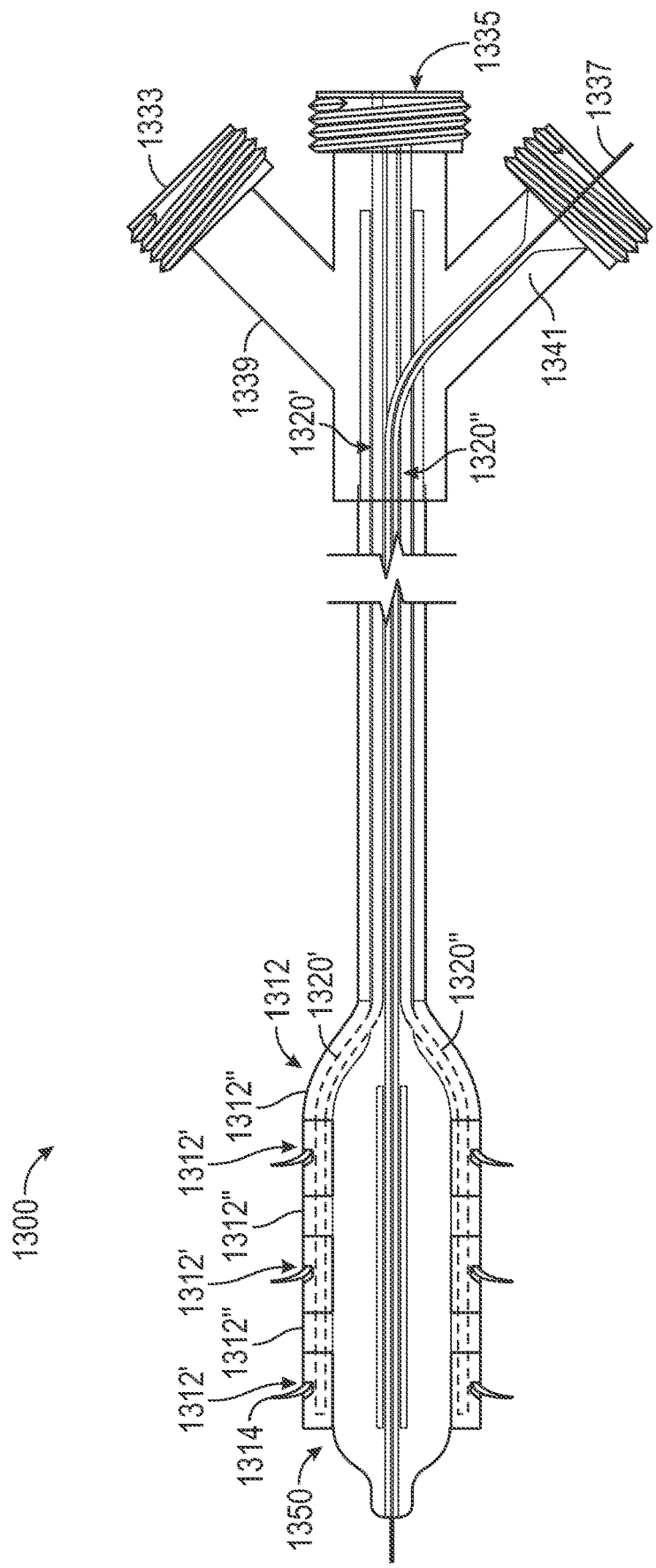
FIG. 13 is a side view illustrating an exemplary infusion device, including a proximal region positioned to be disposed outside of a patient.

FIG. 13 illustrates an exemplary DEBC 1300 shown with expandable member 1350 in an expanded configuration and a plurality of needles 1314 (only one of which is labeled) deployed from openings in spines 1312 (only one spine is labeled, and there may be additional spines and associated needles). In this example, the spines include first regions 1312' at and around the locations where needles extend through openings therefrom, and regions 1312" axially adjacent and optionally in between first regions 1312'. First regions 1312' may be considered to include the spine openings from which the needles extend. First regions 1312' may be less flexible than regions 1312". This arrangement may provide sufficient stiffness to the spine region where the needle extends therefrom, helping the needle pierce through tissue (or calcification), while regions 1312" can provide more flexibility for tracking and delivery. Any of the spines herein may include first and second regions with different stiffness as in the example of FIG. 13.

As is set forth herein, the scaffolds of the DEBCs herein may be secured to the inflatable member, either directly or indirectly. As is set forth herein, the scaffolds of the DEBCs (including the spines) may be secured to the inflatable member along their entire length, or less than their entire length. In some devices, the individual spines may be secured to the inflatable balloon at a plurality of axially spaced sections or regions along its length, and not directly secured to the inflatable member at one or more axially-spaced sections or regions along its length. For example only, with respect to FIG. 13, the plurality of spines may be secured to the inflatable member 1350 in regions 1312', but not in regions 1312". Not directly securing the spines to the inflatable member in regions 1312" may allow for more movement and flexibility in the more flexible regions 1312", which may provide more flexibility overall in the region of the scaffold, which may help when delivering the device.

FIG. 13 also illustrates exemplary rail track or needle subassemblies 1320' and 1320" within corresponding spines, which may include a plurality of needles and one or more fluid lumens, which are described in more detail herein (there may be as many subassemblies as there are spines).

FIG. 13 also illustrates an exemplary proximal region of DEBC 1300. The proximal region includes an adaptor 1339, which in this example is a three-port adaptor. Adaptor 1339 includes an inflation port 1333 configured to couple to a fluid delivery device (e.g., Inflation Device commonly used with dilatation catheters) to deliver an inflation fluid to inflate expandable member 1350. Adaptor 1339 also houses a guidewire lumen 1341 therein, which is sized and configured to receive guidewire 1337 therein, which may facilitate delivery of any of the DEBCs herein over a guidewire. Adaptor 1339 also includes an actuator coupling region 1335, which may be sized and configured to couple to an actuation member, an example of which is described in more detail with respect to FIG. 14.

Any other feature from any other DEBCs herein may be incorporated into the example in FIG. 13, and vice versa.

Figure 14:
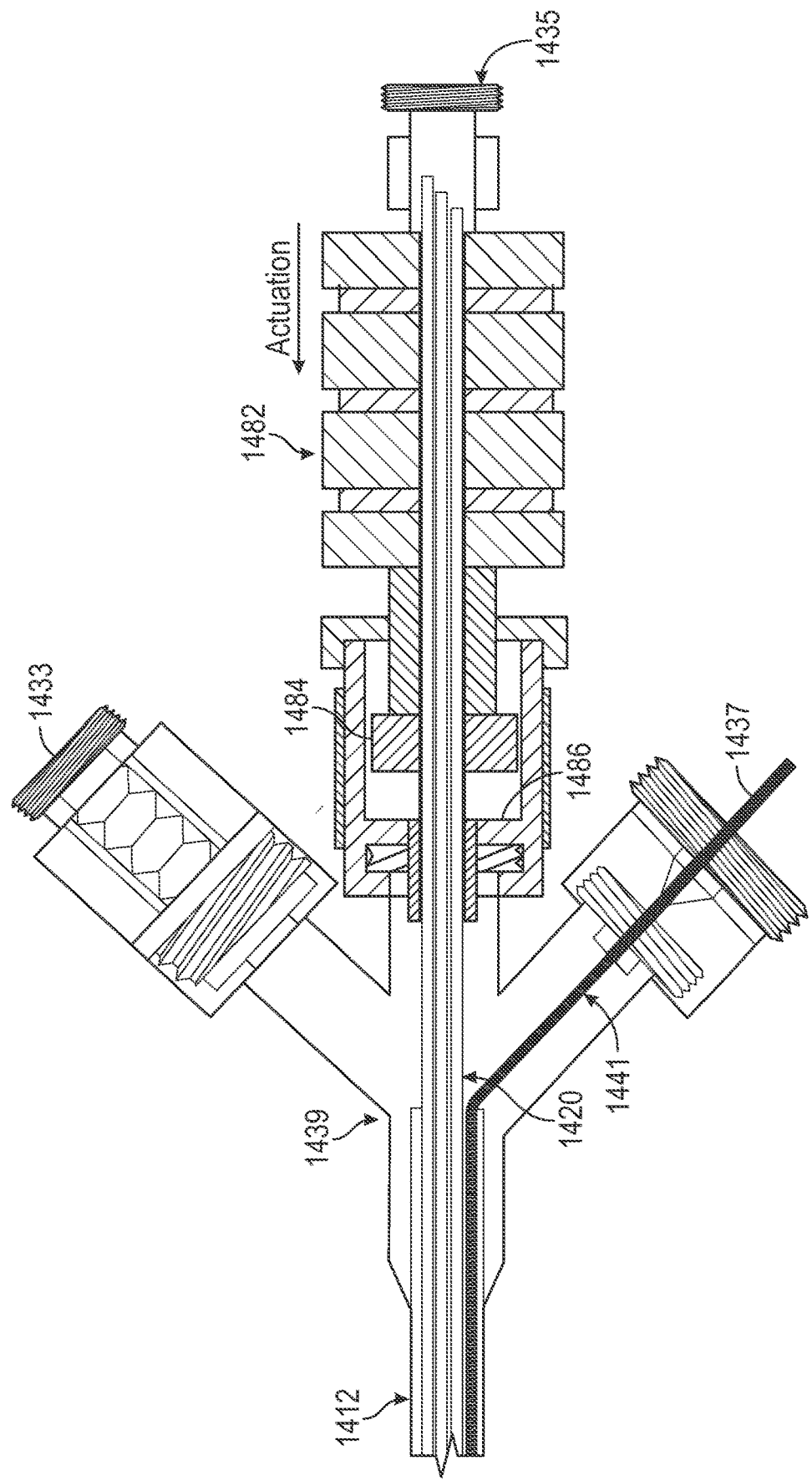
FIG. 14 is a side view of an exemplary proximal region of an exemplary infusion device, including an exemplary actuator.

FIG. 14 illustrates an exemplary proximal region of an DEBC, any features of which may be incorporated into any of the DEBCs herein. The proximal region includes optionally three-port adaptor 1439, which may house a guidewire lumen 1441 therein that is adapted to receive a guidewire 1437 therein for guidewire delivery. In this example, the proximal handle region includes an actuator 1482 that is in operational communication with the rail track subassemblies to facilitate axial movement thereof, which are generally labeled 1420, but it is understand there may be two or more (such as the three that are shown). The rail track subassemblies 1420 may have proximal ends that are attached (directly or indirectly) to an inner surface of actuator 1482, such as by using any suitable bonding technique, which thereby causes the rail track subassemblies to move distally upon distal actuation of the actuator 1482, to thereby deploy the needles from the spine openings. In this example, actuator 1482 has a plunger type construction, with a distal member 1484 that is sized to interface with inner surface 1486 to stop further movement of the actuator 1482. The handle, rail(s) and needles can also be configured, positioned and arranged to enable deployment of the needles by moving the rail track proximally relative to the spine, wherein the needles in their undeployed state reside distal to the spine openings with the needle tips oriented or facing generally proximally and, when the rail track is moved proximally, the needles exit the spine openings. This stop mechanism is an example of a stop mechanism that is adapted to control the distal travel of the actuator 1482. This can be set at any desired distance to control the amount of needle deployment. The proximal portion also includes infusion port 1435, which is adapted to be coupled to a source of therapeutic and/or diagnostic agent to facilitate delivery thereof through the one or more delivery lumens and to the needles. A proximal region of an exemplary spine 1412 is also shown in FIG. 14, but it is understood that there may be as many spines as there are rail track sub-assemblies. Any other feature from any other DEBCs herein may be incorporated into the example in FIG. 14, and vice versa.

Figure 15A:
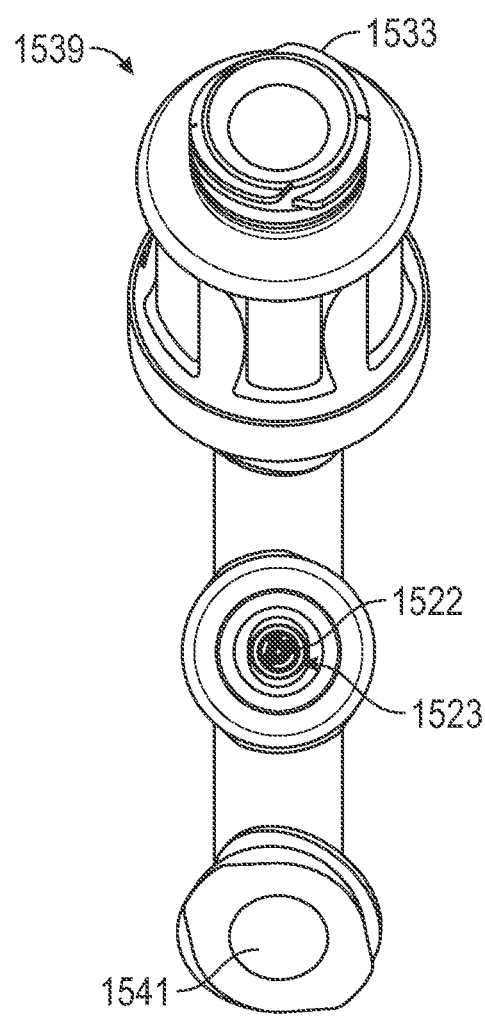
FIGS. 15A and 15B are proximal end views of a proximal external region of an exemplary infusion device.
Figure 15B:
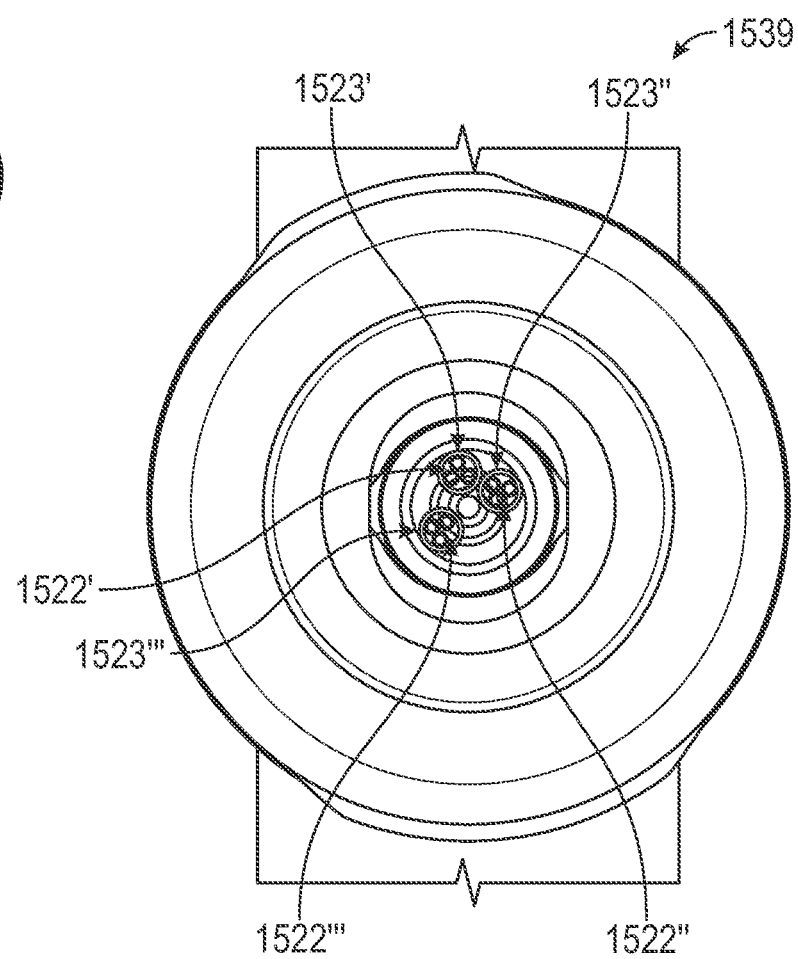

FIGS. 15A and 15B are proximal and cross-sectional end views of the proximal region illustrated in FIG. 14, including three-port adaptor 1539, with FIG. 15B highlighting proximal ends of rails 1523 and fluid delivery lumens 1522 housed therein. FIG. 15A illustrates inflation port 1533 generally, guidewire lumen 1541 generally, and proximal ends of rails 1523 and fluid delivery lumens 1522 therein. FIG. 15B focuses on exemplary rails 1523', 1523", and 1523'". In this example each rail 1523 houses therein three fluid delivery lumens, 1522', 1522", and 1522'", respectively. The fluid delivery lumens are in fluid communication with the needles, such that a therapeutic agent may be delivered into the proximal ends of the fluid lumens 1522 and to the needles. Any other feature from any other DEBCs herein may be incorporated into the example in FIGS. 15A and 15B, and vice versa.

Any of the needles may be deployable using an external component (that remains outside the patient) that is operatively coupled to one or more needles of the DEBC. In some exemplary embodiments, all of the needles in the DEBC are deployable in unison, and may be operatively coupled to a common deployment actuator, an example of which is shown in FIG. 14 and described above. It is understood that other mechanisms may be used to deploy the needles, either in unison or not in unison. For example, the external portion (which may be referred to herein as a proximal region of the DEBC) may have more than one actuator, each of which may control a subsection of the plurality of needles.

Figure 22:
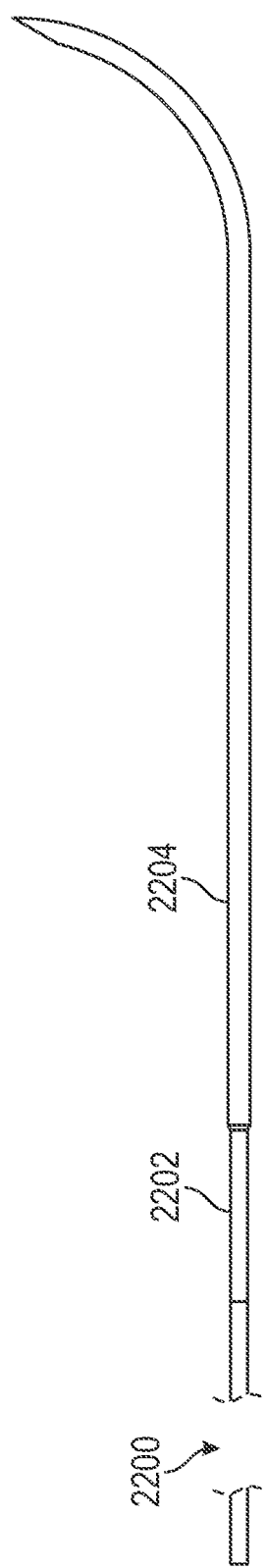
FIG. 22 illustrates an exemplary coupling between a needle and an infusion lumen.

Any of the needles herein may be referred to as microneedles, and may be comprised of nitinol, stainless steel, and/or a combination of nitinol, stainless steel, and other materials that adapt the needle to be able penetrate into the vessel wall. Any of the needles herein may range in length from 0.1 mm-3 mm and in size from 20 gauge to 38 gauge, for example. For clarity, the lengths and/or size of individual needles may vary relative to any adjacent needles, either in the same spine or different spines. Furthermore, the relative inner diameter, outer diameter, and wall thickness of the individual needles may be uniform relative to adjacent needles, or they may vary relative to any adjacent needles, either in the same spine or different spines. Additionally, any of the needles herein may have at least one of an inner diameter ("ID") and an outer diameter ("OD") that varies along the length of the needle. A representative illustration of a needle with a stepped down outer diameter to facilitate coupling with an infusion lumen is shown in FIG. 22, which is described in further detail below.

In any of the DEBCs herein, the expandable infusion scaffold may comprise two or more infusion lumens extending in a longitudinal (axial direction; proximal-distal) or non-longitudinal pattern along at least a portion of the length of the balloon. Longitudinal in this context refers generally to at least a portion of an infusion lumen that is parallel with a longitudinal axis of inflatable balloon. In some embodiments, the scaffold may comprise two or more infusion lumens extending in a non-longitudinal pattern along at least a portion of the length of the balloon. Any of the infusion lumens herein may have one or more portions that extend longitudinally and one or more portions that extend non-longitudinally. Examples of a non-longitudinal configuration or pattern in this context include a spiral or helical configuration or other non-longitudinal pattern. For the sake of illustration, the following describes infusion lumens that run or extend longitudinally (axially) along at least a portion of the length of the scaffold. "Longitudinally" (and derivative thereof) and "axially" (and derivatives thereof) are generally used synonymously herein. "Linear" may also be used with longitudinal and axial when made in reference to a linear longitudinal or linear axial configuration, such as if parallel to a longitudinal (or long) axis of the DEBC or an inflatable member.

The DEBCs herein may include, when expanded, a plurality of infusion lumens or spines that are disposed about an outer surface of a cylindrical region of the balloon, wherein the plurality of infusion lumens have a spiral or helical configuration about the cylindrical region of the balloon. Any additional feature of any of the DEBCs herein may be included as well.

In some exemplary embodiments herein (such as in FIG. 6A-6F), the microneedles are secured (e.g., directly attached, or attached via one or more intermediate components) to a rail or other elongate member that is loaded into and disposed in the infusion spine. Exemplary benefits of this design include, but are not limited to, 1) protection of the balloon, guide catheter, delivery sheath, vessel wall, or any other structure in proximity to the microneedles by isolating the sharp needle points during delivery to the lesion site and/or removal from the lesion site; 2) the ability to use the scaffold to facilitate controlled dilation and optionally scoring of the vessel wall to improve vessel compliance during balloon dilatation ahead of deploying the infusion needles; and/or 3) added structural support during deployment of the needles. Needles that are secured to tracks or other elongate members herein may also enable the depth of needle deployment to be controlled or adjusted. For example, any of the rails herein may be in operable communication with an external portion (e.g., as shown in FIG. 13-15B), wherein one or more actuators (e.g., rotatable knobs, axially movable sliders) in the external portion may be adapted to be actuated to control the relative degree of motion of the rail track subassembly (e.g., axial translation), and thereby control the length of the needles that exit radially or somewhat radially outward from the infusion spine.

Any of the microneedles herein may also have one or more side holes or ports formed therein in addition to or alternatively to a port at a distal end of the needle. In variations of any of the embodiments herein, the needles may only have side holes and may not have a distal hole. Side ports or holes may enable concurrent infusion at more than one depth within the vessel wall. Exemplary benefits of having one or more side holes in the needle include, but are not limited to, enabling local delivery of the therapeutic agent or diagnostic agent into the medial layer of the vessel as well as deep into the adventitial layer of the vessel and/or ensuring delivery of therapy to non-uniform vessel wall thickness as in the case of non-concentric lesions.

Any of the rails herein may also be referred to as a support shaft, any of which may be solid or have a lumen therein. The rails herein may be made of any number of potential materials such as nitinol or stainless steel onto which the needles can be bonded or attached (directly or indirectly), and which may optionally be slatted or laser cut along at least a portion thereof to provide enhanced trackability. Additionally, any of the rails herein may be comprised of more than one type of material along the length of the device. Any of the individual needles herein may include a first end that may be straight or linear and the other free end may be pre-formed (e.g., heat set) to take a perpendicular or near perpendicular configuration (e.g. 60-120 degrees) to the surface of the vessel when the needle is in its deployed state. A straight or linear section of a needle may be individually secured (e.g., directly attached) to an axially moveable member such as a rail, allowing the free end to be free to deform and assume its deployed shape (e.g., pre-set shape) as it exits the infusion spine opening.

Axial spacing between needles may be optimized based on the desired anatomical coverage of the agent within the vessel wall, along with spacing to facilitate optimal delivery and trackability of the DEBC to the target lesion.

In any of the embodiments herein, any number of distal ends of individual infusion spines may be axially staggered (or axially offset, or spaced axially) relative to any other infusion spine distal ends, which may enhance trackability of the distal end region of the device. Alternatively, in any of the embodiments herein, at least two lumens may have distal ends that are axially aligned, but those distal ends may be axially spaced from one or more other infusion lumen distal ends. In this fashion, any number of infusion lumen distal ends may be axially aligned or axially staggered relative to any number of other infusion lumen distal ends. In the exemplary embodiment shown in FIG. 1, the infusion lumens are circumferentially staggered or off-set around or about the scaffold and inflatable member, as well as having distal ends that are axially offset. In the exemplary embodiment shown in FIG. 5, the infusion lumens are circumferentially staggered or off-set around or about the scaffold and inflatable member, but axially aligned at the distal ends.

As described elsewhere herein, the individual rail remains inside the respective infusion spine, serving as a mechanism by which to advance and retract the microneedles. One or more openings (or windows) in the infusion spine provide a pathway for the microneedle(s) to exit the infusion spine and can also be adapted to function as added structural support as the needle penetrates into the vessel wall. Any of the infusion spine windows or openings herein (which may also be described as "space," and as such may be defined by surrounding structure in the infusion spine, for example) may be configured with a slight tented structure around the perimeter thereof to offer additional guidance and structural support, or they may be configured to be flat or concave relative to the cross-section of the infusion spine. The infusion spines herein may also be configured to have a structure located just distal or just proximal to an opening or window (the structure may define the surface(s) of the "opening") that is configured to function as an additional intraluminal guide or ramp as the needle advances out of the infusion spine opening, examples of which are described below.

In any of the examples herein, advancement and retracting of one or more rails or support shafts, to which one or more microneedles are secured (directly or indirectly), may be enabled through a mechanical turn dial (or any other rotatable handle actuator) or any other mechanical actuation mechanism with intuitive settings to guide the user during deployment and retraction of the microneedles.

In any of the examples herein, after the microneedles are deployed, infusion may be initiated using, for example only, a controlled mechanism of volume delivery based on the lesion length and desired volume of agent infusion.

In any of the examples herein, the number of needles per infusion spine may be of any desired number, inclusive but not limited to the range of two to fifty microneedles per infusion spine. In some embodiments, the microneedles may be attached or otherwise secured by techniques such as welding, soldering, mechanical crimping, adhesive, or other techniques to a rail and/or fluid delivery lumen. The needles herein may be bonded directly to a fluid delivery lumen, or they be bonded to one or more intermediate elements such as a coupler. Further, as is described in more details elsewhere herein, the depth of needle deployment may be controlled or adjusted, for example, by utilizing one or more controls in an external portion of the device that may be adapted to control the relative degree of motion of the rail track or support shaft subassembly and thereby control the length of needle that exits radially or somewhat radially outward from the device.

In some examples herein, each needle associated with a spine is in fluid communication with an individual and separate fluid delivery lumen. This may offer several advantages including, but not limited to 1) enabling more tightly controlled dosing through the individual infusion needles; 2) enabling more tightly controlled direction of fluid delivery, and 3) enabling simultaneous delivery of separate complementary therapy agents.

Figure 9:
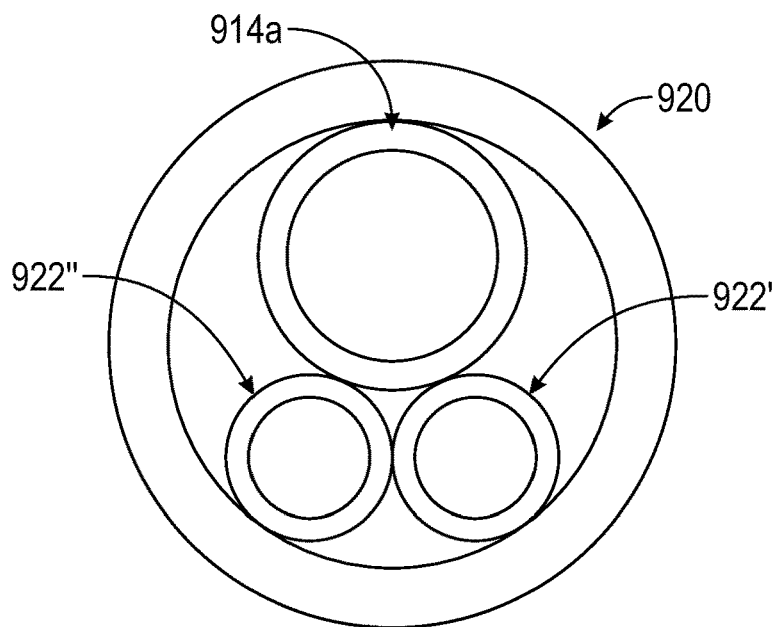
FIG. 9 illustrates an exemplary cross section of an exemplary needle or rail track sub-assembly.
Figure 10:
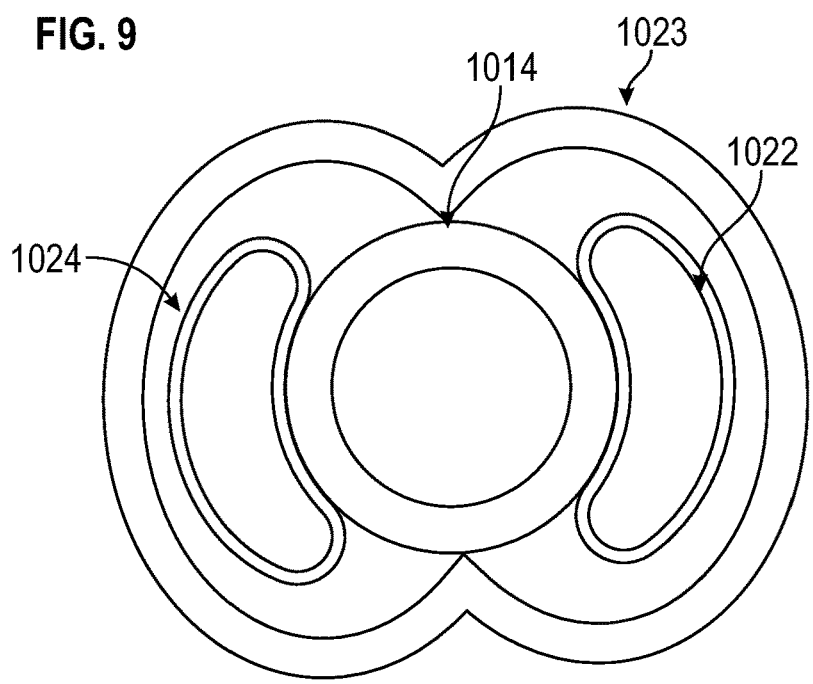
FIG. 10 illustrates an exemplary cross section of an exemplary needle or rail track sub-assembly.

Any of the fluid delivery lumens herein may have one of a variety of cross-sectional shapes inclusive of, but not limited to, round and kidney shaped. This may be done to help reduce the overall profile of the needle assembly without compromising the volume of agent that can be infused through the lumen(s). FIG. 10 is a sectional view through one of three needles associated with a particular spine (spine not shown for clarity). FIG. 10 shows exemplary rail 1023, exemplary needle 1014 and fluid delivery lumens 1022 and 1024 that are in fluid communication with a second and third needle, respectively, which are not shown as they are axially spaced from needle 1014. For example only, needle 1014 may be a proximal needle with two additional needles distal to needle 1014. In this example, rail 1023 optionally has a non-circular outer profile along at least a portion of the length as shown, reasons for which may include mechanical crimping for added structural reinforcement between the rail-track and infusion needle. Fluid delivery lumens 1022 and 1024 have non-circular sectional shapes, which in this example can be approximated to kidney shaped, and may be crescent shaped in other embodiments. Alternatively, FIG. 9 illustrates a cross section of a rail track assembly 920 (920 is also pointing to the rail element) including needle 914*a* and fluid delivery lumens 922' and 922", wherein the cross section of the rail and the fluid delivery lumens are circular.

Any of the lumens herein may be comprised of one or more materials inclusive of, but not limited to, polyimide, polymer, nitinol, composite, and/or combination thereof. Any of the fluid delivery lumens and needles within a rail may be secured using a variety of potential techniques such as, without limitation, crimping, welding, soldering, potting, adhesive, or other techniques inclusive of a combination thereof. In any of these embodiments, any single needles may thus be in fluid communication with a unique or distinct fluid delivery lumen that is only in fluid communication with that particular needle and not any other needles. In alternatives, a plurality of needles may be in fluid communication with a first fluid delivery lumen, and a different needle may be in fluid communication with a second fluid delivery lumen.

In some methods of use, the DEBC herein may be delivered over a guidewire to the target location. After the DEBC is delivered to the target location within a vessel, an inflation fluid can be delivered to an inner volume within the inflatable balloon to cause its expansion. This balloon expansion also applies a force to the expandable scaffold, causing the scaffold and spine to radially expand towards the vessel wall. As the balloon expands, the spines of the scaffold (or cover(s)/sleeve(s)) make contact with the vessel wall, optionally scoring the inner surface of the vessel as the balloon expands to improve vessel compliance during balloon dilatation. The needles may then be deployed from the spine opening and through the vessel wall, which is described in more detail elsewhere herein, and optionally by distally advancing one or more rails within the spines. The agent may then be delivered from a fluid source, through the one or more fluid delivery lumens, and out of the one or more needle ports and into the vessel wall optionally including the adventitia. The needles may be retracted by retracting one or more rails, and the DEBC scaffold and inflatable member may then be collapsed. The DEBC may then be deflated and removed from the patient or delivered to another location for a subsequent agent delivery process.

Depending on the method of use of the intravascular apparatus (e.g., DEBC) it may be beneficial for any of the apparatuses herein to include one or more spine securing members that are positioned and configured to help secure the position of the spine relative to the inflatable member. In some embodiments, the spines may be directly attached to the inflatable member, such as with one or more adhesives, and the one or more securing members are positioned and configured to help prevent the spines from detaching or delaminating from the inflatable member. In other embodiments, however, the spines may not be attached to the surface of the balloon, and in these in embodiments the one or more securing members are positioned and configured to more generally help secure the position of the spine relative to the inflatable member. In embodiments in which the spines are not attached to the inflatable member, the spines may be able to move very slightly relative to the inflatable members, while the securing members in these embodiments are still considered to help secure the position of the spine relative to the inflatable member. Intravascular apparatuses herein may optionally have more than one type of spine securing member, which is described in more detail below.

It is understood that the securing members herein may be incorporated into the apparatuses not necessarily as a requirement to secure the position of the spine relative to the inflatable member, but rather as added reassurance that the position of the spine will be maintained relative to the inflatable member during delivery and use. For example, in some applications, the apparatus may be delivered along a tortuous pathway, which may increase the likelihood of separation (e.g., delamination) between the spine and inflatable member. The securing members herein may be implemented to help ensure that one or more spines do not become separated from the inflatable member (in embodiments in which they are secured to the inflatable member).

In general, the securing members herein are disposed radially outside of at least a portion of the spines, and optionally in a location where the spines extend about an outer cylindrical surface of the inflatable member. In this context, and for clarity, the securing members may not be disposed radially outside of the radially outermost surface of the spines (although they may be), but rather they may be disposed radially outside of at least some portion of the spine structure, examples of which are described below. The position and configuration of the securing member relative to the spine helps secure the position of the spine relative to the inflatable member. It is also understood that spine securing members may be used with inflatable members that do not have a cylindrical region when inflated.

Figure 17A:
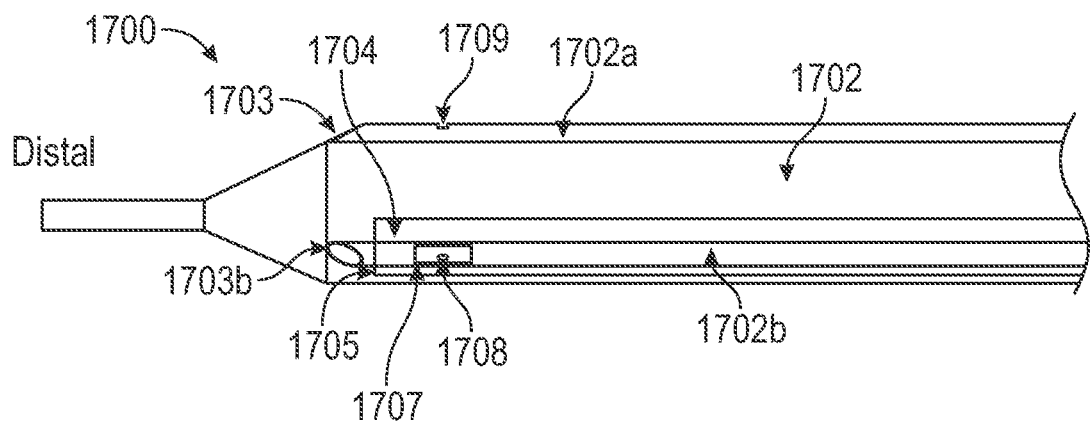
FIGS. 17A and 17B are side views of an exemplary apparatus that includes an exemplary securing member that comprises a cover.
Figure 17B:
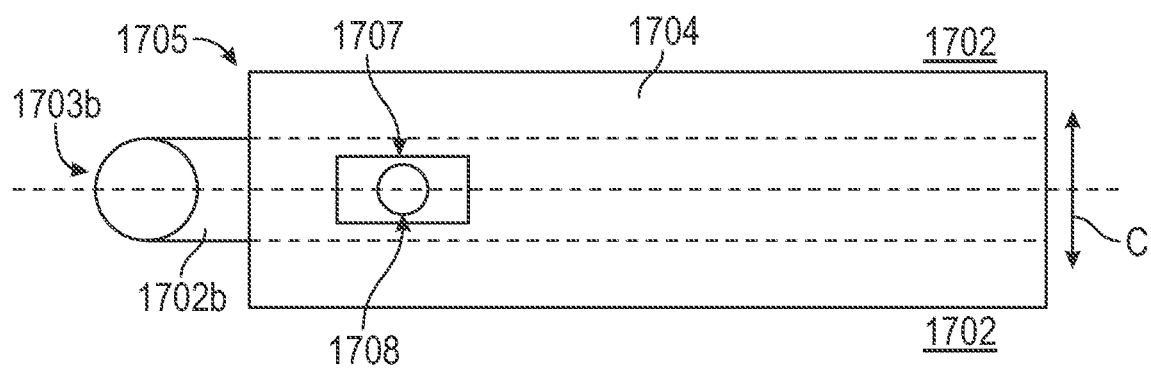
Figure 17C:
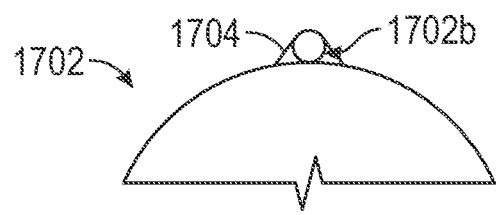
FIG. 17C is an end view of an exemplary apparatus that includes an exemplary securing member that comprises a cover.

FIGS. 17A-17C illustrate a distal region of an exemplary apparatus 1700, which may also include any of the suitable features of any other intravascular apparatus described herein, and vice versa. Apparatus 1700 includes one or more spine securing members. FIG. 17A is a side view showing apparatus after inflatable member 1702 has been inflated, including expandable scaffold spines 1702a and 1702b disposed about a cylindrically shaped region of inflatable member 1702. An optional one or more additional spines on the other side of the apparatus is not visible, and which may be the same as spines 1702a and 1702b in any or all ways. In this embodiment, the spines include distal ends 1703a and 1703b that extend generally to the distal end of the cylindrically shaped region of the inflatable member, as shown. Distal ends 1703a and 1703b may, however, be proximal to the distal end of the cylindrical region of the inflatable member.

Only one radial needle opening, 1708 and 1709 respectively, are shown in each spine (from which the needles are deployed), but it is of course understood that the spines may include more than one opening, examples of which are provided herein.

Apparatus 1700 includes spine securing member 1704, which in this embodiment is a thin cover member disposed radially about an outermost surface of the spine along a portion of the length of the spine. Circumferential regions of the cover securing member 1704 are, in this embodiment, secured to the inflatable member, which is shown in the distal sectional view of FIG. 17C. Securing member 1704 and inflatable member 1702 essentially sandwich spine 1702b (shown in FIG. 17C), while securing member 1704 acts as a radial constraint to help maintain the spine position relative to inflatable member 1702. Any of the "spine securing members" herein may be referred to as a "securing member," and vice versa.

Spine securing member 1704 includes opening or window 1707 at the location of spine radial opening 1708 from which a needle is deployed. Opening 1707 allows a needle to be deployed unencumbered out of spine opening 1708, methods of which are described in more detail herein. In this embodiment, opening 1707 may be formed by removing material from securing member 1704, such as by cutting material to form opening 1707. The term opening in this context refers generally to a lack of material disposed radially outside of a portion of the spine. Securing members may include a plurality of openings, wherein there is an opening disposed at the location of any spine radial opening.

Securing member 1704 is an example of a securing member adapted as a cover, at least a portion of which is disposed about at least a portion of a radially outermost surface of the spine.

The spine securing members herein that are disposed about a radially outermost surface of the spine (e.g., securing member 1704) may be relatively thin, such as, without limitation, having a wall thickness from 0.0005 inches to 0.01 inches.

The spine securing members herein may optionally comprise one or more polymeric materials, such as, without limitation, one or more polyimides, one or more polyurethanes, one or more PEBAX® polymers, including any combination thereof.

Circumferential regions or sides of securing member 1704 are secured to inflatable member 1702. In this context, an example of a circumferential direction "C" is labeled in FIG. 17B, which refers generally to a direction or path that is not parallel with a long axis, which is shown in the dashed line in FIG. 17B. A "circumferential" direction in this context does not require a direction orthogonal to the long axis, but rather may also refer to other angles relative to the long axis.

Securing members disposed about the radially outermost surface of the spines may optionally be formed by extrusion, wherein the openings may be subsequently formed (e.g., cutting material away). Alternatively, securing members disposed about the radially outermost surface of the spines may optionally be formed by dip-coating, wherein masks may be placed on the spine(s) at the location wherein openings or windows (e.g., opening 1707; or key windows, which are described below) are desired.

While not shown in FIG. 17A, additional cover securing members may of course be disposed about each of the other spines, and which may be the same as securing member 1704 in any or all ways.

Spine securing members herein that are disposed radially outside of a radially outermost surface of one or more spines may extend along at least a portion of the length of the spines. Distal ends of the securing members may be disposed distal to the distal end of the spine, axially aligned with the distal end of the spine, or disposed proximal to the distal end of the spine (e.g., as in FIG. 17A). Proximal ends of these securing members are generally distal to the proximal ends of the spine, but they may extend to the proximal ends of the spines. Proximal ends of the spines herein may be disposed at a variety of locations along the length of the entire device. For example, any of the spines herein may extend to a proximal region of the device, such as is shown in exemplary FIG. 14. Alternatively, any of the spines herein may have proximal ends that terminate at any location along and within the catheter shaft, including at a distal end of the catheter shaft, and may even terminate slightly distal to a distal end of the catheter shaft. Any of the spines herein may have lengths such that the spine extends mainly along at least a portion of the length of an inflatable member and not significantly or at all within the outer catheter shaft. In some embodiments, these spine securing members may extend along the entire length or substantially the entire length of the spines where the spines extend about an outer cylindrical surface of the inflatable balloon. In some embodiments, spine securing members do not extend along an entire distal tapered region of a balloon, but they may extend along a proximal tapered region of the balloon. In some embodiments, the spine securing members do not extend along a proximal tapered region of a balloon.

Figure 18A:
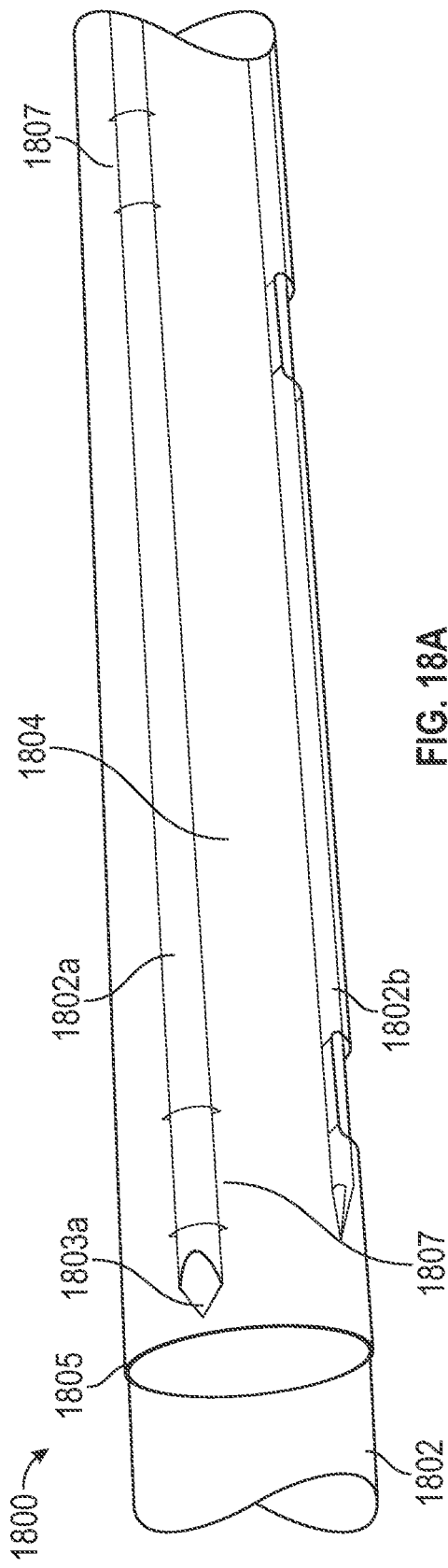
FIGS. 18A and 18B are perspective side views of an exemplary apparatus that includes an exemplary securing member that comprises a cover.
Figure 18B:
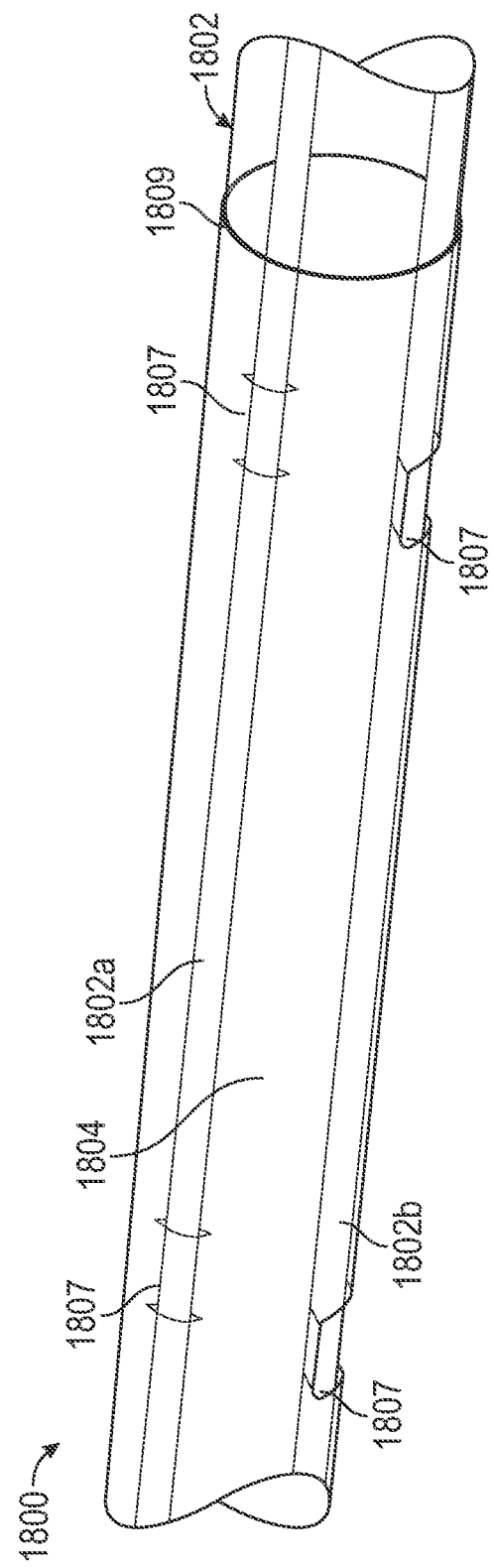

FIGS. 18A and 18B illustrate an exemplary intravascular apparatus 1800, which may also include any of the suitable features of any other intravascular apparatus described herein, and vice versa. FIG. 18A illustrates a distal region of the apparatus, while FIG. 18B illustrates a proximal region thereof (although there may be some overlap between the two figures). FIGS. 18A and 18B illustrate the apparatus in an expanded configurations in which an inflatable balloon 1802 is inflated and expandable spines 1802a and 1802b of the expandable scaffold have been expanded. Apparatus 1800 may also include any of the features of any of the one or more axially move needle assemblies herein, including the deployable needles and rails.

In this exemplary embodiment, apparatus 1800 includes a cover securing member 1804 that extends about radially outermost portions of the scaffold spines. Securing member 1804 may be considered to extend circumferentially about the inflatable member 1802 and the spines. Securing member 1804 also includes a plurality of openings 1807 which are disposed at the locations of the spine radial openings (which are not shown for clarity, but which may be any of the spines radial openings herein).

In this exemplary apparatus 1800, openings 1807 are optionally not formed by removing the entire section of the material at the opening. Instead, two relatively short axially-spaced slits are made (during manufacture), which may be orthogonal to a long axis of the securing member. The region that is axially between the two slits may be moved or pushed radially inward relative to adjacent sections of the securing member, which creates a pathway for the spine to be advanced during manufacturing. A portion of the securing member is under the spine (relative to a long axis) at the location of the securing member opening.

During manufacture, the spine may be advanced over the securing member section that was moved radially inward. The balloon may then be expanded, and the securing member and the balloon may be bonded at one or more locations 1810 (see sectional FIGS. 18C and 18D) circumferentially in between the spines to secure the balloon to the securing member and help stabilize spines therebetween. FIG. 18C illustrates a section of apparatus 1800 where the securing member 1804 extends radially about the outermost portions of the scaffold spines and circumferentially about the inflatable member 1802. FIG. 18D illustrates a section where the securing member 1804 is under, or radially within, the spines and circumferentially about the inflatable member 1802. It is understood that the relative dimensions in FIGS. 18C and 18D are not necessarily to scale. For example, the thicknesses of inflatable member 1802 and securing member 1804 are exaggerated in FIGS. 18C and 18D to more clearly indicate their positions relative to each other and to the spines. In practice, the thicknesses of inflatable member 1802 and securing member 1804 are generally, particularly relative to the dimensions of the spines, much less than the thicknesses shown in FIGS. 18C and 18D. For example only, exemplary securing members herein may have wall thicknesses from 0.0005 inches to 0.01 inches.

In any of the embodiments herein, the outer securing member may optionally be attached to the spines herein (e.g., solvent bonded, adhered with adhesive, etc.), although alternatively the outer securing member may not be attached to the spines.

Exemplary securing member 1804 has a proximal end 1809 shown in FIG. 18B that does not extend to the proximal end of the balloon, and in this example does not extend along a proximal tapered region of the balloon. In variations, however, the proximal end of the securing member may extend further proximally, such as over a tapered region of the balloon.

Exemplary securing member 1804 has a distal end 1805 shown in FIG. 18A that does not extend to the distal end of the balloon, and in this example does not extend along a distal tapered region of the balloon. In variations, however, the distal end of the securing member may extend further distally, such as over a distal tapered region of the balloon.

Exemplary securing member 1804 has a distal end 1805 that extends slightly distally beyond the distal end 1803a of spine 1802a, but in other embodiments it may not extend distally beyond the distal ends of the spines, and may optionally be disposed proximal to the distal ends of the spines.

In this example, securing member 1804 is attached to inflatable member 1802 at one or more locations 1810, which are circumferentially in between adjacent spines.

In any of the embodiments herein, the outer securing member may alternatively be disposed over some or all of the scaffold such that some or all of the needles exit and pierce through the outer securing member into their deployed state.

Depending on the design of the apparatus, it may be beneficial to help secure the position of at least a distal region of the spine relative to the inflatable member. For example, and without limitation, a distal end of a spine may be susceptible to being separated from an inflatable member. In some embodiments herein, apparatuses herein may include one or more securing members that extend into an inner lumen defined by each of the one or more spines.

Securing members that extend into an inner spine lumen may help provide additional stability to the distal region of the spines.

FIGS. 19A-19C illustrates an exemplary apparatus 1900 that includes a plurality of securing members that are each disposed within distal region of the spine lumens. Apparatus 1900 includes inflatable member 1902 and scaffold spines 1902a and 1902b (although additional spines may be included). Needles are shown in deployed states from spine radial openings, details of which are described elsewhere herein. In this embodiment spine securing member 1904 includes a plurality of legs 1920, each of which includes a proximal end 1921 (only one of which is visible and labeled) that is disposed within a distal region of a spine, as shown. Legs 1920 of securing member 1904 do not extend as far proximally as the needles, as shown.

Apparatus 1900 also includes distal tip 1950, which in this example includes a cap 1952 disposed about distal region of legs 1920, which helps secure the distal ends of the legs. The cap 1952 can be thermally reflowed or mechanically formed or reshaped to create a smooth transition over the exposed portion of the legs to the distal tip of the catheter. Guidewire lumen 1940 also extends to tip 1950, and helps provide inner radial support to the distal ends of legs 1920. In variations, securing member 1904 may have a distal end wherein the legs are attached, either as a monolithic structure, or separate legs that are physically attached to each other. For example, the securing member may be made from a tubular starting material, wherein cuts may be made to form the legs, while leaving the distal end as a tubular structure. Proximal ends of the legs are adapted to radially expand as the inflatable member expands, and in this example extend along a tapered section of the inflatable member.

FIG. 19C is a sectional view through section A-A from FIG. 19A, showing a single leg within a lumen of spine 1902a. Securing members herein are described as being disposed radially outside of at least a portion of the spine. While legs are not disposed radially outside of the entire spine, legs 1920 herein are disposed radially outside of spine portion 1962, which is shown in FIGS. 19A and 19C. That is, the securing members in this example are disposed radially outside of an inner portion of the spines. It is thus understood that a securing member that is within a spine lumen is disposed radially outside of a portion of the spine.

Securing member 1904 may comprise, without limitation, one or more of a metal, a metal alloy (e.g., stainless steel, nitinol), a polymeric material, or any combination thereof.

Any of the apparatuses herein may include more than one type of securing member. For example, and without limitation, any of the apparatuses herein may include securing members that extend into the spine lumens (e.g., legs 1920 of securing member 1904) as well as securing member(s) that extend radially about at least a portion of a radially outermost surface of the spines (e.g., securing member(s) 1704, securing member 1804). FIGS. 20A and 20B illustrate an alternative embodiment in which apparatus 2000 includes inflatable member 2002, an expandable scaffold with a plurality of spines, and securing members 2004a, 2004b and 2004c (which, together, are referred to generally as securing members 2004). Securing member 2004c is not visible in FIGS. 20A and 20B. Securing members 2004 are each configured as a sleeve that extends circumferentially about the entirety of one of the spines. Alternatively stated, each spine is disposed within one of the sleeved securing members 2004. The securing members 2004 can be comprised of one or more materials that have properties that enable adhesive or thermal bonding to the inflatable member. Securing members 2004 may optionally have any feature of any of the securing members herein that extend about a radially outermost surface of at least a portion of a spine.

Securing members 2004 may each be considered to be tubular members circumferentially surrounding at least a portion of one of the plurality of spines. In this example, securing members 2004 each includes one or more openings or windows therein, but there are regions or sections of the securing members, along their lengths, that do not include openings or windows and completely circumferentially surround the spine. Even when the sleeved securing members herein (e.g., securing members 2004) include one or more openings or windows, the sleeved securing members are considered to be completely circumferentially surrounding at least a portion of the spines.

One or more regions of the sleeves may be bonded to the inflatable member. For example, sleeve securing members herein may comprise a material that allows the sleeve to be adhesively and/or thermally bonded to the inflatable member. In some merely exemplary embodiments, a layer of adhesive between a radially inner portion of the sleeve may secure the sleeve to the inflatable member. Alternatively, or additionally, an adhesive may be applied further circumferentially along a portion of the sides of the sleeves, essentially creating fillets between the inflatable member and sleeve on the sides of the sleeve. Regardless of the particular location of an adhesive (if adhesive is included), bonding between the sleeve and the inflatable member acts to help secure the position of the spine (which is disposed within the sleeve) relative to the inflatable member, and thus acts as a spine securing member.

Apparatus 2000 further includes a second securing member (which is a different type of securing member than securing members 2004), which comprises a plurality of legs 2020 that are positioned inside the distal regions of the spine lumens. Legs 2020 may include any feature of legs 1920 shown in FIGS. 19A-19C. Apparatus 2000 also includes tip 2050, which may include any feature of tip 1950 described herein, including a cap 1952 that secures the legs of a securing member. The guidewire lumen also extends into tip 2050, and a guidewire 2060 is shown extending distally from a distal end of the guidewire lumen.

Securing members 2004 of apparatus 2000 also optionally include one or more key openings or windows 2017, which are at the location of one or more spine keys 2019, which are described below. Securing members 2004 are examples of securing members that include a plurality of openings, wherein at least one opening is at the location of a needle radial opening (as shown) and optionally at least a second opening that is disposed at the location of one or more spine keys. The securing members openings are generally associated with a spine feature, whether a needle opening or an alignment member (e.g., key). In this example, each key opening 2017 is at the location of a plurality of spine keys 2019, though optionally each key opening may be at the location of a single spine key as described in more detail herein.

One aspect of this disclosure is related to apparatuses that include one or more alignment features that help maintain circumferential alignment between the distal tips of the needles and the spine radial openings to ensure that the needle tips are circumferentially aligned with the spine openings as the needle assemblies are moved axially, which ensures that the needles are properly deployed from the openings. If a needle tip is not circumferentially aligned with the spine radial opening, the needle can miss the opening circumferentially, and the needle may not deploy.

In some embodiments, the rails herein may optionally include one or more first alignment members, while the corresponding spine in which the rail is disposed may include one or more second alignment members, which in some embodiments may comprise one or more spine keys. The one or more first alignment members can be sized, positioned, and configured to interface with the one or more second alignment members to maintain circumferential alignment of the corresponding plurality of needles and the plurality of radial openings as the rail is axially advanced within the spine, to thereby facilitate deployment of the plurality of needles out of the plurality of radial openings. While the disclosure provides examples of first and second interface members, it is understood that other types of interface members may be used without departing from the spirit of this aspect of the disclosure.

FIGS. 21A-21D illustrate exemplary interface members, which may be incorporated into any of the apparatuses herein. FIG. 21A is a side view and illustrates only a portion of apparatus 2100. Only one spine 2102 and one axially movable needle assembly are shown (including rail 2160 and needle 2170), but it is of course understood that apparatus 2100 may include any feature of any of the apparatuses herein (including multiple spines and multiple needles associated with each spine).

Rail 2160 includes first alignment member 2163, which in this embodiment comprises a slot. Spine 2102 includes second alignment members 2113, which in this embodiment include a plurality of keys that are sized, positioned, and configured to interface with the rail slot 2163. As shown in FIG. 21A, first alignment member 2163 includes a flattened surface in the side view. The keys in this example extend radially inward relative to the outer spine surface, as shown, and also have a flattened surface that interfaces with the flattened surface of the slot.

FIG. 21B illustrates a portion of the exemplary spine 2102, and illustrates a merely exemplary way in which the spine alignment member(s) 2113 may be formed during manufacturing, which in this example are spine keys, or keyed elements. Spine 2102 may be a tubular member (e.g., nitinol, stainless steel tube), and a cut 2117 may be made in the tube, while a section 2115 may be left uncut. Cut 2117 separates a portion of the tubular material, which in this example can be deformed radially inward, as shown, to form a keyed element 2113. The spine may include one or more keys 2113, or similar second alignment members. The uncut region 2115 may be considered monolithic with the adjacent spine region. Spine 2102 also illustrates exemplary laser cut regions 2119 that are axially spaced from the key region of the spine. The laser cut region may include any pattern (regular or irregular) of cuts that increase the flexibility of that region of the spine.

As shown, the keys in this example are not orthogonal to the long axis, but in variations they may optionally extend radially inward at different angles, including orthogonally.

In alternative designs, the rails herein may comprise one or more keys that extend radially outwards towards the spine, and the corresponding spine may include one or more slots shaped to interface with the rail keys to help maintain circumferential alignment of the needles and spine radial openings.

One aspect of this disclosure is related to apparatuses that include spine(s) with one or more needle deployment guides extending into the spine lumen and positioned and configured to guide the needle out of the corresponding radial opening of the spine. Any feature of any of the apparatuses herein may be included in this aspect, but it is understood that this aspect need not include any particular feature of the apparatuses herein. For example, needle guides may be implemented in an apparatus with or without circumferential alignment members and circumferential alignment members may be implemented in an apparatus with or without needle guides.

FIGS. 21C and 21D illustrate an exemplary spine 2102 with an exemplary needle deployment guide 2121, which in this exemplary may be formed generally the same way as the spine keys described herein. Needle guide 2121 is positioned and configured to help guide a needle radially out of the spine radial opening and prevent the needle from being moved axially beyond the radial opening and missing the spine opening. In this example, and as shown, needle guide 2121 extends radially inward and proximally relative to outer surface of spine 2102. As shown, in this example, a portion of needle deployment guide 2121 is disposed at a distal end of the corresponding spine radial opening, and a second portion of the needle deployment guide extends radially inward and proximally therefrom. In this example, the uncut, monolithic region, is at the distal end of the needle opening. FIG. 21D illustrates needle 2170 in an undeployed state, while FIG. 21C illustrates needle 2170 in a deployed state, after having been guided by needle deployment guide 2121.

The needle deployment guides may also be described as extending radially inward at an angle greater than zero relative to the outer surface of the spine, which does not require that the guide is flat, and in fact the needle deployment guides herein may have variety of configurations as long as they help guide the needle out of the spine opening. For example, they may be curved ramps, flat ramps, curvilinear, etc.

In alternative designs, however, the needle guide may be disposed at a proximal end of the needle opening, and may extend radially inward and distally. For example, and as described in more detail herein with reference to FIG. 14, the apparatus may be configured such that the rail is adapted to be moved proximally within the spine to deploy the needles, in which case the needle guide would be positioned at the proximal end of the spine opening to facilitate needle deployment in this variation.

As an alternative embodiment of FIG. 6E, FIG. 22 illustrates a side view of an exemplary infusion lumen 2200 disposed over a smaller diameter stepped-down proximal portion of an exemplary needle 2204 (stepped down region at least partially disposed within infusion lumen 2200), which may be incorporated into any of the needle couplings herein. The stepped down needle region may include, for example, a vertical step, a gradual taper, or a combination of both. Other components of the needle sub-assembly or rail track sub-assembly are not shown for clarity. Infusion lumen 2200 and needle 2204 axially overlap in overlap region 2202. By way of example only, the infusion lumen may comprise one or more polymeric materials, such as a polyimide or polyetheretherketone. Alternatively, the needles may extend proximally and function as the infusion lumen, wherein the needle may extend the full length of the catheter, or until the needle interfaces with an axially moveable rail, wherein the rail lumen functions as the common fluid infusion lumen, which is described herein.

What is claimed is:

1. An intravascular apparatus, comprising:
 an inflatable balloon having an inflated cylindrical configuration;
 an expandable infusion scaffold comprising at least first and second expandable infusion spines, each of the at least first and second infusion spines defining a lumen therein and each including two or more spaced apart radial openings therethrough, wherein the expandable infusion scaffold is adapted and positioned about the inflatable balloon such that inflation of the balloon causes the scaffold to radially expand, the at least first and second infusion spines extending about an outer cylindrical surface of the inflatable balloon when the inflatable balloon is in an inflated state;

a plurality of movable needles assemblies, each one of the plurality of movable assemblies disposed in one of the at least first and second expandable infusion spines and movable within and relative to the infusion spine, each of the plurality of movable assemblies comprising a rail that includes a rail lumen, a plurality of needles, and one or more fluid delivery lumens within the rail lumen that are in fluid communication with the plurality of needles, wherein the plurality of needles are coupled to the rail such that movement of the rail within the corresponding infusion spine moves the plurality of the needles as a group relative to the infusion spine between undeployed configurations in which each of the plurality of needles are housed within the infusion spine and deployed configurations in which each of the plurality of needles extends generally radially out of one of the radial openings in the infusion spine for delivery of an agent into a wall of a target vessel; and at least one spine securing member that is disposed radially outside of at least a portion of the at least first and second spines in a location where the at least first and second spines extend about the outer cylindrical surface of the inflatable balloon, wherein a first spine securing member is disposed radially outside of a radially outermost surface of at least one of the first and second spines, and a second spine securing member is disposed within a distal region of at least one of the first and second spine lumens.

2. The apparatus of claim 1, wherein the first spine securing member comprises a sleeve that is bonded to the inflatable balloon along a radially inner portion of the sleeve, and wherein at least a portion of one of the spines is disposed within the sleeve.

3. The apparatus of claim 1, wherein the second spine securing member is disposed within a distal region of each of the spine lumens.

4. The apparatus of claim 2, further comprising a plurality of sleeves, each of which is bonded to the inflatable balloon along a radially inner portion of the sleeve, and wherein at least a portion of each of the spines is disposed within one of the plurality of sleeves.

5. An intravascular apparatus, comprising:

an inflatable balloon having an inflated cylindrical configuration;

an expandable infusion scaffold comprising at least first and second expandable infusion spines, each of the at least first and second infusion spines defining a lumen therein and each including two or more spaced apart radial openings therethrough, wherein the expandable infusion scaffold is adapted and positioned about the inflatable balloon such that inflation of the balloon causes the scaffold to radially expand, the at least first and second infusion spines extending about an outer cylindrical surface of the inflatable balloon when the inflatable balloon is in an inflated state;

a plurality of movable needles assemblies, each one of the plurality of movable assemblies disposed in one of the at least first and second expandable infusion spines and movable within and relative to the infusion spine, each of the plurality of movable assemblies comprising a rail that includes a rail lumen, a plurality of needles, and one or more fluid delivery lumens within the rail lumen that are in fluid communication with the plurality of needles, wherein the plurality of needles are coupled to the rail such that movement of the rail within the corresponding infusion spine moves the plurality of the needles as a group relative to the infusion spine between undeployed configurations in which each of the plurality of needles are housed within the infusion spine and deployed configurations in which each of the plurality of needles extends generally radially out of one of the radial openings in the infusion spine for delivery of an agent into a wall of a target vessel; and at least one spine securing member that is disposed radially outside of at least a portion of the at least first and second spines in a location where the at least first and second spines extend about the outer cylindrical surface of the inflatable balloon, wherein the at least one spine securing member comprises a sleeve that is disposed radially outside of at least a portion of a radially outermost surface of the at least first and second spines, wherein the sleeve is bonded to the inflatable balloon along a radially inner portion of the sleeve, and wherein at least a portion of one of the spines is disposed within the sleeve.

6. The apparatus of claim 5, wherein the sleeve comprises a first material and the inflatable member comprises a second material, wherein the first material and the second material facilitate one or more of adhesive or thermal bonding between the sleeve and the inflatable member.

7. The apparatus of claim 5, wherein the at least one spine securing member comprises a plurality of sleeves, each of which is bonded to the inflatable balloon along a radially inner portion of the sleeve, and wherein at least a portion of each of the at least first and second spines is disposed within one of the plurality of sleeves.

8. The apparatus of claim 5, wherein the sleeve comprises one or more polymeric materials, optionally comprising polyurethane or PEBAX.

9. The apparatus of claim 5, wherein the sleeve extends along substantially the entire length of the spine where the spine extends about the outer cylindrical surface of the inflatable balloon.

10. The apparatus of claim 6, wherein the first material is the same as the second material.

11. The apparatus of claim 10, wherein the first material and the second material comprise a polyurethane.

12. The apparatus of claim 9, wherein the sleeve extends about a proximal tapered section of the inflatable balloon.

13. The apparatus of claim 9, wherein the sleeve does not extend about a proximal tapered section of the inflatable balloon.

14. An intravascular apparatus, comprising:

an inflatable balloon having an inflated cylindrical configuration;

an expandable infusion scaffold comprising at least first and second expandable infusion spines, each of the at least first and second infusion spines defining a lumen therein and each including two or more spaced apart radial openings therethrough,
  wherein the expandable infusion scaffold is adapted and positioned about the inflatable balloon such that inflation of the balloon causes the scaffold to radially expand, the at least first and second infusion spines extending about an outer cylindrical surface of the inflatable balloon when the inflatable balloon is in an inflated state;
a plurality of movable needles assemblies, each one of the plurality of movable assemblies disposed in one of the at least first and second expandable infusion spines and movable within and relative to the infusion spine, each of the plurality of movable assemblies comprising
  a rail that includes a rail lumen, a plurality of needles, and one or more fluid delivery lumens within the rail lumen that are in fluid communication with the plurality of needles,
  wherein the plurality of needles are coupled to the rail such that movement of the rail within the corresponding infusion spine moves the plurality of the needles as a group relative to the infusion spine between undeployed configurations in which each of the plurality of needles are housed within the infusion spine and deployed configurations in which each of the plurality of needles extends generally radially out of one of the radial openings in the infusion spine for delivery of an agent into a wall of a target vessel; and
at least one spine securing member that is disposed radially outside of at least a portion of the at least first and second spines in a location where the at least first and second spines extend about the outer cylindrical surface of the inflatable balloon,
  wherein the at least one spine securing member comprises a plurality of spine securing members, wherein each of the plurality of spine securing members is disposed within a distal region of one of the spine lumens.

15. The apparatus of claim 14, wherein the plurality of spine securing members do not extend as far proximally as a distal most needle associated with the corresponding spine.

16. The apparatus of claim 14, wherein the plurality of spine securing members are coupled together at their respective distal ends.

17. The apparatus of claim 14, wherein distal ends of the plurality of spine securing members are secured by an outer tip member.

18. The apparatus of claim 14, wherein the plurality of spine securing members each have distal ends that are not directly coupled to any other spine securing member.

19. The apparatus of claim 14, wherein each of the plurality of spine securing members extends along a distal tapered region of the inflated balloon.

20. The apparatus of claim 14, wherein the plurality of spine securing members comprise at least one of a metallic material or a polymeric material.

21. The apparatus of claim 14, wherein proximal regions of the plurality of spine securing members are adapted to expand radially outward as the balloon is inflated.

* * * * *